(12) United States Patent
Weiss et al.

(10) Patent No.: US 10,590,054 B2
(45) Date of Patent: Mar. 17, 2020

(54) METHODS AND SYSTEMS TO FORM PROPYLENE CHLOROHYDRIN FROM DICHLOROPROPANE USING LEWIS ACID

(71) Applicant: Calera Corporation, Moss Landing, CA (US)

(72) Inventors: Michael Joseph Weiss, Los Gatos, CA (US); Kyle Self, San Jose, CA (US); Thomas A Albrecht, Santa Clara, CA (US); Margarete K Leclerc, Mountain View, CA (US)

(73) Assignee: Calera Corporation, Moss Landing, CA (US)

(*) Notice: Subject to any disclaimer, the term of this patent is extended or adjusted under 35 U.S.C. 154(b) by 0 days.

(21) Appl. No.: 16/424,878

(22) Filed: May 29, 2019

(65) Prior Publication Data

US 2019/0367435 A1 Dec. 5, 2019

Related U.S. Application Data

(60) Provisional application No. 62/678,038, filed on May 30, 2018.

(51) Int. Cl.
*C07C 29/09* (2006.01)
*C07C 31/36* (2006.01)
*C07C 31/34* (2006.01)
*C07C 17/02* (2006.01)

(52) U.S. Cl.
CPC .............. *C07C 29/09* (2013.01); *C07C 17/02* (2013.01); *C07C 31/34* (2013.01); *C07C 31/36* (2013.01)

(58) Field of Classification Search
CPC ........ C07C 29/09; C07C 29/64; C07C 29/124; C07C 31/34; C07C 31/36; C07C 17/02
See application file for complete search history.

(56) References Cited

U.S. PATENT DOCUMENTS

| 2,752,402 | A | | 6/1956 | Pye |
| 2,792,342 | A | | 5/1957 | Tuwiner |
| 2,999,887 | A | | 9/1961 | Finlay et al. |
| 3,079,444 | A | | 2/1963 | Jacobowsky et al. |
| 3,214,481 | A | | 10/1965 | Heinemann et al. |
| 3,214,482 | A | | 10/1965 | Caropreso et al. |
| 3,277,189 | A | * | 10/1966 | Bromberg ............... C07C 31/36 568/850 |
| 3,397,226 | A | | 8/1968 | Fenton |

(Continued)

FOREIGN PATENT DOCUMENTS

| CA | 1339833 C | 4/1998 |
| CN | 103238233 B | 9/2015 |

(Continued)

OTHER PUBLICATIONS

Acquah, et al. The electrochlorination of aliphatic hydrocarbons. J. Appl. Chem. Biotechnol. 1972; 22:1195-1200.

(Continued)

*Primary Examiner* — Yate' K Cutliff
(74) *Attorney, Agent, or Firm* — Calera Corporation; Vandana Bansal

(57) ABSTRACT

There are provided methods and systems to form propylene chlorohydrin by hydrolysis of dichloropropane in presence of Lewis acid and to further form propylene oxide from the propylene chlorohydrin.

22 Claims, 4 Drawing Sheets

(56) References Cited

U.S. PATENT DOCUMENTS

| | | |
|---|---|---|
| 3,427,235 A | 2/1969 | Joseph |
| 3,437,712 A | 4/1969 | Robert et al. |
| 3,461,180 A | 8/1969 | Heinz et al. |
| 3,510,532 A | 5/1970 | Frank et al. |
| 3,607,420 A | 9/1971 | Leonard |
| 3,634,330 A | 1/1972 | Max et al. |
| 3,635,803 A | 1/1972 | Thomas et al. |
| 3,691,239 A | 9/1972 | Homer et al. |
| 3,723,544 A * | 3/1973 | Roberts, Jr. ............ C07C 17/361 568/841 |
| 3,845,144 A * | 10/1974 | Bartholome et al. ... C07C 29/66 568/850 |
| 3,884,984 A * | 5/1975 | Hirose ..................... C07C 29/64 568/850 |
| 3,985,794 A | 10/1976 | Calcagno et al. |
| 4,008,133 A | 2/1977 | Gelbein et al. |
| 4,108,752 A | 8/1978 | Pohto et al. |
| 4,111,779 A | 9/1978 | Seko et al. |
| 4,126,526 A | 11/1978 | Kwon et al. |
| 4,190,508 A | 2/1980 | Kametani et al. |
| 4,256,719 A | 3/1981 | Van Andel |
| 4,277,405 A | 7/1981 | Apanel |
| 4,319,977 A | 3/1982 | Wortley |
| 4,324,625 A | 4/1982 | Cumbo |
| 4,376,019 A | 3/1983 | Gamlen et al. |
| 4,379,019 A | 4/1983 | Pool |
| 4,394,227 A | 7/1983 | Jaeger et al. |
| 4,402,811 A | 9/1983 | Klotz et al. |
| 4,555,317 A | 11/1985 | Nicolas et al. |
| 4,581,116 A | 4/1986 | Plowman et al. |
| 4,595,469 A | 6/1986 | Foller |
| 4,643,818 A | 2/1987 | Seko et al. |
| 4,672,142 A | 6/1987 | Hundeck et al. |
| 4,726,887 A | 2/1988 | McIntyre |
| 4,767,519 A | 8/1988 | De Nora |
| 4,814,420 A | 3/1989 | Brunelle et al. |
| 4,834,847 A | 5/1989 | McIntyre |
| 4,908,198 A | 3/1990 | Weinberg |
| 4,950,368 A | 8/1990 | Weinberg et al. |
| 5,050,603 A | 9/1991 | Stokes et al. |
| 5,296,107 A | 3/1994 | Harrison |
| 5,364,508 A | 11/1994 | Weres et al. |
| 5,437,771 A | 8/1995 | Shimamune et al. |
| 5,523,425 A * | 6/1996 | Pech ...................... C07C 29/66 549/521 |
| 5,532,389 A | 7/1996 | Trent et al. |
| 5,595,641 A | 1/1997 | Traini et al. |
| 5,891,318 A | 4/1999 | Freire et al. |
| 5,932,750 A | 8/1999 | Hayashi et al. |
| 6,043,400 A * | 3/2000 | Jorge ...................... C01B 11/06 568/812 |
| 6,117,286 A | 9/2000 | Shimamune et al. |
| 6,146,787 A | 11/2000 | Harrup et al. |
| 6,368,473 B1 | 4/2002 | Furuya et al. |
| 6,372,102 B1 | 4/2002 | Sakata et al. |
| 6,383,349 B1 | 5/2002 | Sakata et al. |
| 6,395,153 B1 | 5/2002 | Matousek et al. |
| 6,591,199 B2 | 7/2003 | Tremblay et al. |
| 7,157,609 B2 * | 1/2007 | Tanaka ................... C07C 29/64 568/841 |
| 7,404,878 B2 | 7/2008 | Katayama et al. |
| 7,569,083 B2 | 8/2009 | Katayama et al. |
| 7,616,006 B2 | 11/2009 | Tremblay et al. |
| 7,658,835 B2 | 2/2010 | Gestermann et al. |
| 7,708,867 B2 | 5/2010 | Yamada et al. |
| 7,735,274 B2 | 6/2010 | Constantz et al. |
| 7,744,761 B2 | 6/2010 | Constantz et al. |
| 7,749,476 B2 | 7/2010 | Constantz et al. |
| 7,753,618 B2 | 7/2010 | Constantz et al. |
| 7,754,169 B2 | 7/2010 | Constantz et al. |
| 7,771,684 B2 | 8/2010 | Constantz et al. |
| 7,790,012 B2 | 9/2010 | Kirk et al. |
| 7,797,137 B2 | 9/2010 | Veillette et al. |
| 7,815,880 B2 | 10/2010 | Constantz et al. |
| 7,818,276 B2 | 10/2010 | Veillette et al. |
| 7,829,053 B2 | 11/2010 | Constantz et al. |
| 7,837,842 B1 | 11/2010 | Mayers, Sr. et al. |
| 7,875,163 B2 | 1/2011 | Gilliam et al. |
| 7,887,694 B2 | 2/2011 | Constantz et al. |
| 7,906,028 B2 | 3/2011 | Constantz et al. |
| 7,914,652 B2 | 3/2011 | Yamada et al. |
| 7,914,685 B2 | 3/2011 | Constantz et al. |
| 7,922,809 B1 | 4/2011 | Constantz et al. |
| 7,931,809 B2 | 4/2011 | Constantz et al. |
| 7,933,511 B2 | 4/2011 | Masuki |
| 7,939,336 B2 | 5/2011 | Constantz et al. |
| 7,966,250 B2 | 6/2011 | Constantz et al. |
| 7,993,500 B2 | 8/2011 | Gilliam et al. |
| 7,993,511 B2 | 8/2011 | Gilliam et al. |
| 8,006,446 B2 | 8/2011 | Constantz et al. |
| 8,062,418 B2 | 11/2011 | Constantz et al. |
| 8,114,214 B2 | 2/2012 | Constantz et al. |
| 8,114,265 B2 | 2/2012 | Berriah et al. |
| 8,137,455 B1 | 3/2012 | Constantz et al. |
| 8,152,987 B2 | 4/2012 | Tremblay et al. |
| 8,197,649 B2 | 6/2012 | Saiki et al. |
| 8,357,270 B2 | 1/2013 | Gilliam et al. |
| 8,894,830 B2 | 11/2014 | Gilliam et al. |
| 8,940,139 B2 | 1/2015 | Asaumi et al. |
| 9,108,844 B2 | 8/2015 | Huss |
| 9,175,410 B2 | 11/2015 | Izawa et al. |
| 9,181,624 B2 | 11/2015 | Sugiyama et al. |
| 9,187,834 B2 | 11/2015 | Albrecht et al. |
| 9,187,835 B2 | 11/2015 | Albrecht et al. |
| 9,200,375 B2 | 12/2015 | Gilliam et al. |
| 9,273,404 B2 | 3/2016 | Bulan et al. |
| 9,828,313 B2 | 11/2017 | Weiss et al. |
| 9,957,621 B2 | 5/2018 | Albrecht et al. |
| 9,957,623 B2 | 5/2018 | Gilliam et al. |
| 2003/0150819 A1 | 8/2003 | Iseki et al. |
| 2004/0251199 A1 | 12/2004 | Benavides |
| 2004/0267063 A1 | 12/2004 | Harth et al. |
| 2005/0244689 A1 | 11/2005 | Horiguchi et al. |
| 2006/0124445 A1 | 6/2006 | Labrecque et al. |
| 2006/0149102 A1 | 7/2006 | Voight et al. |
| 2007/0014709 A1 | 1/2007 | Moyes et al. |
| 2007/0292762 A1 | 12/2007 | Johnson |
| 2008/0023339 A1 | 1/2008 | Berggren et al. |
| 2008/0029404 A1 | 2/2008 | Weber et al. |
| 2008/0223727 A1 | 9/2008 | Oloman et al. |
| 2008/0275279 A1 | 11/2008 | Podkolzin et al. |
| 2009/0001020 A1 | 1/2009 | Constantz et al. |
| 2009/0020044 A1 | 1/2009 | Constantz et al. |
| 2009/0029199 A1 | 1/2009 | Tao |
| 2009/0087698 A1 | 4/2009 | Huth et al. |
| 2009/0169452 A1 | 7/2009 | Constantz et al. |
| 2009/0202410 A1 | 8/2009 | Kawatra et al. |
| 2009/0301352 A1 | 12/2009 | Constantz et al. |
| 2009/0325031 A1 | 12/2009 | Sugawara et al. |
| 2010/0000444 A1 | 1/2010 | Constantz et al. |
| 2010/0024686 A1 | 2/2010 | Constantz et al. |
| 2010/0032347 A1 | 2/2010 | Ring et al. |
| 2010/0041927 A1 | 2/2010 | Olver et al. |
| 2010/0051469 A1 | 3/2010 | Stolberg |
| 2010/0051859 A1 | 3/2010 | House et al. |
| 2010/0063902 A1 | 3/2010 | Constantz et al. |
| 2010/0077691 A1 | 4/2010 | Constantz et al. |
| 2010/0077922 A1 | 4/2010 | Constantz et al. |
| 2010/0083880 A1 | 4/2010 | Constantz et al. |
| 2010/0084280 A1 | 4/2010 | Gilliam et al. |
| 2010/0108537 A1 | 5/2010 | Perego et al. |
| 2010/0111810 A1 | 5/2010 | Constantz et al. |
| 2010/0116683 A1 | 5/2010 | Gilliam et al. |
| 2010/0132556 A1 | 6/2010 | Constantz et al. |
| 2010/0132591 A1 | 6/2010 | Constantz et al. |
| 2010/0135865 A1 | 6/2010 | Constantz et al. |
| 2010/0135882 A1 | 6/2010 | Constantz et al. |
| 2010/0140103 A1 | 6/2010 | Gilliam et al. |
| 2010/0144521 A1 | 6/2010 | Constantz et al. |
| 2010/0150802 A1 | 6/2010 | Gilliam et al. |
| 2010/0154679 A1 | 6/2010 | Constantz et al. |
| 2010/0155258 A1 | 6/2010 | Kirk et al. |
| 2010/0158786 A1 | 6/2010 | Constantz et al. |

(56) References Cited

U.S. PATENT DOCUMENTS

| | | |
|---|---|---|
| 2010/0170805 A1 | 7/2010 | Krafft et al. |
| 2010/0179302 A1 | 7/2010 | Krafft et al. |
| 2010/0196104 A1 | 8/2010 | Constantz et al. |
| 2010/0200419 A1 | 8/2010 | Gilliam et al. |
| 2010/0219373 A1 | 9/2010 | Seeker et al. |
| 2010/0224503 A1 | 9/2010 | Kirk et al. |
| 2010/0229725 A1 | 9/2010 | Farsad et al. |
| 2010/0230293 A1 | 9/2010 | Gilliam et al. |
| 2010/0230830 A1 | 9/2010 | Farsad et al. |
| 2010/0236242 A1 | 9/2010 | Farsad et al. |
| 2010/0239467 A1 | 9/2010 | Constantz et al. |
| 2010/0239487 A1 | 9/2010 | Constantz et al. |
| 2010/0247410 A1 | 9/2010 | Constantz et al. |
| 2010/0258035 A1 | 10/2010 | Constantz et al. |
| 2010/0258450 A1 | 10/2010 | Burtch |
| 2010/0258506 A1 | 10/2010 | Berkowitz et al. |
| 2010/0270167 A1 | 10/2010 | McFarland |
| 2010/0276299 A1 | 11/2010 | Kelly et al. |
| 2010/0290967 A1 | 11/2010 | Detournay et al. |
| 2010/0313793 A1 | 12/2010 | Constantz et al. |
| 2010/0313794 A1 | 12/2010 | Constantz et al. |
| 2010/0319586 A1 | 12/2010 | Blount et al. |
| 2010/0326328 A1 | 12/2010 | Constantz et al. |
| 2011/0005938 A1 | 1/2011 | Wolf et al. |
| 2011/0028765 A1 | 2/2011 | Mehta |
| 2011/0030586 A1 | 2/2011 | Constantz et al. |
| 2011/0030957 A1 | 2/2011 | Constantz et al. |
| 2011/0033239 A1 | 2/2011 | Constantz et al. |
| 2011/0035154 A1 | 2/2011 | Kendall et al. |
| 2011/0036728 A1 | 2/2011 | Farsad |
| 2011/0042230 A1 | 2/2011 | Gilliam et al. |
| 2011/0054084 A1 | 3/2011 | Constantz et al. |
| 2011/0059000 A1 | 3/2011 | Constantz et al. |
| 2011/0067600 A1 | 3/2011 | Constantz et al. |
| 2011/0067603 A1 | 3/2011 | Constantz et al. |
| 2011/0067605 A1 | 3/2011 | Constantz et al. |
| 2011/0071309 A1 | 3/2011 | Constantz et al. |
| 2011/0076587 A1 | 3/2011 | Wang et al. |
| 2011/0079515 A1 | 4/2011 | Gilliam et al. |
| 2011/0081585 A1 | 4/2011 | Montgomery |
| 2011/0083968 A1 | 4/2011 | Gilliam et al. |
| 2011/0091366 A1 | 4/2011 | Kendall et al. |
| 2011/0091955 A1 | 4/2011 | Constantz et al. |
| 2011/0120888 A1 | 5/2011 | James et al. |
| 2011/0132234 A1 | 6/2011 | Constantz et al. |
| 2011/0147227 A1 | 6/2011 | Gilliam et al. |
| 2011/0152580 A1 | 6/2011 | Hook et al. |
| 2011/0203489 A1 | 8/2011 | Constantz et al. |
| 2011/0226989 A9 | 9/2011 | Seeker et al. |
| 2011/0240916 A1 | 10/2011 | Constantz et al. |
| 2011/0247336 A9 | 10/2011 | Farsad et al. |
| 2011/0269990 A1 | 11/2011 | Honda et al. |
| 2011/0277474 A1 | 11/2011 | Constantz et al. |
| 2011/0277670 A1 | 11/2011 | Self et al. |
| 2011/0315561 A1 | 12/2011 | Rabaey et al. |
| 2012/0000789 A1 | 1/2012 | Turek et al. |
| 2012/0003125 A1 | 1/2012 | Madokoro et al. |
| 2012/0152804 A1 | 6/2012 | Koseoglu et al. |
| 2012/0292196 A1 | 11/2012 | Albrecht et al. |
| 2012/0292197 A1 | 11/2012 | Albrecht et al. |
| 2013/0206606 A1 | 8/2013 | Gilliam et al. |
| 2013/0240372 A1 | 9/2013 | Bulan et al. |
| 2014/0353146 A1 | 12/2014 | Gilliam et al. |
| 2015/0038750 A1 | 2/2015 | Weiss et al. |
| 2015/0337443 A1 | 11/2015 | Albrecht et al. |
| 2015/0361564 A1 | 12/2015 | Albrecht et al. |
| 2016/0040304 A1 | 2/2016 | Albrecht et al. |
| 2016/0060774 A1 | 3/2016 | Gilliam et al. |
| 2016/0076156 A1 | 3/2016 | Albrecht et al. |
| 2016/0108529 A1 | 4/2016 | Albrecht et al. |
| 2016/0230291 A1 | 8/2016 | Albrecht et al. |
| 2017/0073823 A1 | 3/2017 | Albrecht et al. |
| 2017/0121832 A1 | 5/2017 | Albrecht et al. |
| 2018/0044267 A1 | 2/2018 | Weiss et al. |
| 2018/0245223 A1 | 8/2018 | Self et al. |
| 2018/0347056 A1* | 12/2018 | Self ........................... C25B 3/06 |

FOREIGN PATENT DOCUMENTS

| | | |
|---|---|---|
| DE | 19614683 A1 | 10/1997 |
| EP | 0039547 A1 | 11/1981 |
| EP | 0039547 B1 | 7/1984 |
| EP | 1362133 A1 | 11/2003 |
| EP | 2253600 A1 | 11/2010 |
| EP | 1362133 B1 | 7/2011 |
| EP | 2697410 B1 | 6/2015 |
| FR | 1539499 A | 9/1968 |
| GB | 812680 A | 4/1959 |
| GB | 1019437 A | 2/1966 |
| GB | 1063175 A | 3/1967 |
| GB | 1063283 A | 3/1967 |
| GB | 1063284 A | 3/1967 |
| GB | 1553819 * | 10/1979 |
| JP | S56169631 A | 12/1981 |
| JP | S5727129 A | 2/1982 |
| JP | S5874624 A | 5/1983 |
| JP | S63293186 A | 11/1988 |
| JP | H0238573 B2 | 8/1990 |
| JP | H0356683 A | 3/1991 |
| JP | H046290 A | 1/1992 |
| JP | H0432594 A | 2/1992 |
| JP | H05214573 A | 8/1993 |
| JP | H1081986 A | 3/1998 |
| JP | H11256385 A | 9/1999 |
| JP | 2000199093 A | 7/2000 |
| JP | 2001262387 A | 9/2001 |
| JP | 2004027267 A | 1/2004 |
| JP | 2005511670 A | 4/2005 |
| JP | 2009299111 A | 12/2009 |
| TW | 201313958 A | 4/2013 |
| WO | WO-2004097073 A1 | 11/2004 |
| WO | WO-2007058472 A1 | 5/2007 |
| WO | WO-2008018928 A2 | 2/2008 |
| WO | WO-2008148055 A1 | 12/2008 |
| WO | WO-2009006295 A2 | 1/2009 |
| WO | WO-2009086460 A1 | 7/2009 |
| WO | WO-2009146436 A1 | 12/2009 |
| WO | WO-2009155378 A1 | 12/2009 |
| WO | WO-2010006242 A1 | 1/2010 |
| WO | WO-2010008896 A1 | 1/2010 |
| WO | WO-2010009273 A1 | 1/2010 |
| WO | WO-2010030826 A1 | 3/2010 |
| WO | WO-2010039903 A1 | 4/2010 |
| WO | WO-2010039909 A1 | 4/2010 |
| WO | WO-2010048457 A1 | 4/2010 |
| WO | WO-2010051458 A1 | 5/2010 |
| WO | WO-2010055152 A1 | 5/2010 |
| WO | WO-2010068924 A1 | 6/2010 |
| WO | WO-2010074686 A1 | 7/2010 |
| WO | WO-2010074687 A1 | 7/2010 |
| WO | WO-2010087823 A1 | 8/2010 |
| WO | WO-2010091029 A1 | 8/2010 |
| WO | WO-2010093713 A1 | 8/2010 |
| WO | WO-2010093716 A1 | 8/2010 |
| WO | WO-2010101953 A1 | 9/2010 |
| WO | WO-2010104989 A1 | 9/2010 |
| WO | WO-2010132863 A1 | 11/2010 |
| WO | WO-2010136744 A1 | 12/2010 |
| WO | WO-2011008223 A1 | 1/2011 |
| WO | WO-2011017609 A1 | 2/2011 |
| WO | WO-2011038076 A1 | 3/2011 |
| WO | WO-2011049996 A1 | 4/2011 |
| WO | WO-2011066293 A1 | 6/2011 |
| WO | WO-2011073621 A1 | 6/2011 |
| WO | WO-2011075680 A1 | 6/2011 |
| WO | WO-2011081681 A1 | 7/2011 |
| WO | WO-2011097468 A2 | 8/2011 |
| WO | WO-2011102868 A1 | 8/2011 |
| WO | WO-2011116236 A2 | 9/2011 |
| WO | WO-2012158969 A1 | 11/2012 |
| WO | WO-2013082811 A1 | 6/2013 |

(56) References Cited

FOREIGN PATENT DOCUMENTS

| WO | WO-2013148216 A1 | 10/2013 |
|---|---|---|
| WO | WO-2015017585 A1 | 2/2015 |
| WO | WO-2018200785 A1 | 11/2018 |

OTHER PUBLICATIONS

Andersson, et al. High power diode laser cladding. Fabricating and Metalworking. Mar. 2014; 24-26.
Benadda, B. et al. 1996. A study of Oxygen Absorption Kinetics in Ionic Cu(I) Aqueous Solutions. Chem. Eng. Technol. 19: 34-38.
Brugger, et al. Complexation of metal ions in brines: application of electronic spectroscopy in the study of the Cu(II)—LiCl—H2O system between 25 and 90°C. Geochimica et Cosmochimica Acta. 2001; 65(16):2691-2708.
Catalytical Associates, Inc. Selective Oxychlorination of Hydrocarbons: A Critical Analysis. Oct. 1982, pp. 15-20.
Constantz, B. "The Risk of Implementing New Regulations on Game-Changing Technology: Sequestering CO2 in the Built Environment" AGU, Sep. 2009; 90(22), Jt. Assem, Suppl., Abstract.
Co-pending U.S. Appl. No. 15/338,235, filed Oct. 28, 2016.
EP16860934.5 Extended European Search Report dated May 9, 2019.
European search report and opinion dated Feb. 25, 2015 for EP Application No. 12785945.2.
European search report and opinion dated May 11, 2015 for EP Application No. 13769321.4.
"European search report with opinion dated Dec. 8, 2016 for EP14832631.7".
"European search report with written opinion dated Feb. 17, 2017 for EP16188593.4".
European search report with written opinion dated Jul. 18, 2017 for EP17150726.
Friend, L. et al. 1974. Liquid-Phase Oxychlorination of Ethylene to Produce Vinyl Chloride. Homogeneous Catalysis. American Chemical Society. Piscataway, N.J. pp. 168-176.
Georgiadou, M. et al. 1998. Modelling of copper etching in aerated chloride solutions. Journal of Applied Electrochemistry. 28: 127-134.
Hine, F. et al. 1970. Mechanism of Oxidation of Cuprous Ion in Hydrochloric Acid Solution by Oxygen. Electrochimica Acta. 15: 769-781.
International search report and written opinion dated May 23, 2013 for PCT/US2013/031064.
International search report and written opinion dated Aug. 14, 2012 for PCT/US2012/038438.
International search report and written opinion dated Oct. 15, 2014 for PCT/US2014/048976.
International search report and written opinion dated Dec. 17, 2015 for PCT/US2015/050196.
"International search report with written opinion dated Jan. 24, 2017 for PCT/US16/59455".
Jhaveri, A.S., et al. 1967. Kinetics of absorption of oxygen in aqueous solutions of cuprous chloride. Chemical Engineering Science. 22: 1-6.
Kinoshita, et al. Mass-Transfer Study of Carbon Felt, Flow-Through Electrode. J. Electrochem. Soc. 1982; 129(9):1993-1997.
Kotora, et al. Selective Additions of Polyhalognated Compounds to Chloro Substituted Ethenes Catalyzed by a Copper Complex. React. Kinet. Catal. Lett. (no month, 1991), vol. 44, No. 2, pp. 415-419.
Krishnamoorthy, et al. Chlorination of substituted aromatics on graphite anode. Asian Journal of Chemistry. 2002; 14(3-4):1801-1803.
Langer, et al. Electrogenerative and Voltameiotic Processes. Ind. Eng. Chem. Process Des. Dev. 1979; 18(4):567-579.
Langer, et al. Electrogenerative Chlorination J. Electrochem. Soc. 1970; 117(4):510-511.
Little, et al. A microstructural study of a supported liquid phase oxychlorination catalyst. Journal of Catalysis 93.1 (1985): 23-29.

Liu, et al. A spectrophotometric study of aqueous copper(I)-chloride complexes in LiCl solutions between 100°C and 250°C. Geochimica et Cosmochimica Acta. 2002; 66(20):3615-3633.
Logager, et al. Oxidation of Ferrous Ions by Ozone in Acidic Solutions. Inorg. Chem. 1992; 31:3523-3529.
Lundstrom, et al Redox potential characteristics of cupric chloride solutions. Hydrometallurgy. 2009; 95:285-289.
Margraf, et al. Copper(II) PMDTA and Copper(II) TMEDA Complexes: Precursors for the Synthesis of Dinuclear Copper(II) Complexes. Inorgancia Chimica Acta (no month, 2005), vol. 358, pp. 1193-1203.
Muddada, et al. Ethylene oxychlorination catalysis: role of metal promoters on activity and selectivity of the process. Department of Chemistry. University of Oslo. Available at https://www.sintef.no/globalassets/project/trondheim_gts/presentasjoner/ethylene-oxychlorination-catalysis---role-of-metal-promoters-on-activity-and-selectivity-of-the-process.pdf. Nov. 3, 2011. Accessed Jan. 17, 2017.
Nijhuis, et al. The Production of Propene Oxide: Catalytic Processes and Recent Developments. Industrial & Engineering Chemistry Research 2006 45 (10), 3447-3459.
Notice of allowance dated Feb. 12, 2018 for U.S. Appl. No. 15/341,260.
Notice of allowance dated Mar. 7, 2018 for U.S. Appl. No. 14/919,281.
Notice of allowance dated Mar. 16, 2018 for U.S. Appl. No. 14/855,262.
Notice of allowance dated Sep. 16, 2015 for U.S. Appl. No. 13/474,599.
Notice of allowance dated Sep. 28, 2017 for U.S. Appl. No. 14/446,791.
Notice of allowance dated Sep. 30, 2015 for U.S. Appl. No. 13/474,598.
Notice of allowance dated Oct. 9, 2015 for U.S. Appl. No. 13/799,131.
Office action dated Feb. 5, 2018 for U.S. Appl. No. 14/855,262.
Office action dated Feb. 8, 2018 for U.S. Appl. No. 14/834,151.
"Office action dated Feb. 9, 2017 for 14/446,791".
Office action dated Aug. 8, 2017 for U.S. Appl. No. 14/876,760.
Office action dated Aug. 10, 2017 for U.S. Appl. No. 14/460,697.
Office action dated Aug. 14, 2015 for U.S. Appl. No. 13/474,599.
Office action dated Aug. 22, 2017 for U.S. Appl. No. 15/341,260.
Office action dated Aug. 26, 2016 for U.S. Appl. No. 14/460,697.
Office action dated Aug. 27, 2015 for U.S. Appl. No. 13/474,598.
Office action dated Sep. 17, 2015 for U.S. Appl. No. 13/799,131.
Office action dated Oct. 19, 2016 for U.S. Appl. No. 14/446,791.
Office action dated Nov. 7, 2017 for U.S. Appl. No. 14/834,151.
Office action dated Nov. 16, 2017 for U.S. Appl. No. 14/814,935.
Office action dated Nov. 16, 2017 for U.S. Appl. No. 15/341,260.
Office action dated Nov. 27, 2017 for U.S. Appl. No. 14/876,760.
Office action dated Dec. 12, 2017 for U.S. Appl. No. 14/460,697.
"Office action dated Dec. 19, 2016 for U.S. Appl. No. 14/460,697".
Office action dated Dec. 21, 2017 for U.S. Appl. No. 14/919,281.
PCT/US2018/029530 International Search Report and Written Opinion dated Jul. 11, 2018.
PCT/US2018/035010 International Search Report and Written Opinion dated Jul. 27, 2018.
Powell, et al. Chemical speciation of environmentally significant metals with inorganic ligands. Pure Appl. Chem. 2007; 79(5):895-950.
Ralph, et al. Mass transport in an electrochemical laboratory filterpress reactor and its enhancement by turbulence promoters. Electrochemica Acta. 1996; 41(4):591-603.
Richey. Chlorohydrins. Kirk-Ohmer Encyclopedia of Chemical Technology. 2000.
Rollin, et al. The electrochemistry of nickel complexes with triphenylphosphine and ethylene in methylpyrrolidinone. Journal of Electroanalytical Chemistry and Interfacial Electrochemistry. 1985; 183(1-2):247-260.
Rorabacher. Electron transfer by copper centers. Chemical Centers. 2004; 104(2):651-698.
Spector, M.L. et al. 1967. Olefin Chlorination in Homogeneous Aqueous Copper Chloride Solutions. Industrial & Engineering Chemistry Process Design and Development. 6(3): 327-331.

(56) References Cited

OTHER PUBLICATIONS

Stanley, et al. Novel Organic Chemical Processes. Proceedings of the Royal Society of London. Series A, Mathematical and Physical Sciences 303.1474 (1968): 259-273.
Trent, D.L., Propylene Oxide. In Kirk-Othmer:Encyclopedia of chemical technology; Wiley: New York, 2001. (Online electronic edition).
U.S. Appl. No. 61/442,573, filed Feb. 14, 2011.
U.S. Appl. No. 15/338,235 Notice of Allowance dated Jan. 24, 2019.
U.S. Appl. No. 15/338,235 Office Action dated Jun. 15, 2018.
Wikipedia definition of "Aqueous Solution". Accessed Jul. 29, 2015. 2 pages.
Wikipedia definition of "Solvent". Accessed Jul. 29, 2015. 14 pages.
Yuan, et al. Direct Electrochemical Synthesis and Crystal Structure of a Copper(II) Complex with a Chiral (S)-2-(diphenylmethanol-1-(2-pyridylmethyl)pyrrolidine. Inorganic Chemistry Communications (no month, 2005), vol. 8, pp. 1014-1017.
Office action dated Feb. 15, 2018 for U.S. Appl. No. 14/876,760.
Office action dated Mar. 2, 2018 for U.S. Appl. No. 14/814,935.
Office action dated Mar. 4, 2015 for U.S. Appl. No. 13/474,598.
Office action dated Mar. 8, 2018 for U.S. Appl. No. 15/341,260.
Office action dated Mar. 14, 2018 for U.S. Appl. No. 14/877,329.
Office action dated Mar. 21, 2018 for U.S. Appl. No. 14/879,525.
Office action dated Apr. 18, 2017 for U.S. Appl. No. 14/460,697.
Office action dated Apr. 23, 2015 for U.S. Appl. No. 13/474,599.
Office action dated Jun. 11, 2015 for U.S. Appl. No. 13/799,131.
Office Action dated Jun. 26, 2017 for U.S. Appl. No. 14/446,791.
Office action dated Jul. 9, 2015 for U.S. Appl. No. 13/474,598.
Office action dated Jul. 19, 2017 for U.S. Appl. No. 14/814,935.
Office action dated Aug. 6, 2015 for U.S. Appl. No. 13/474,598.
Office action dated Aug. 7, 2017 for U.S. Appl. No. 14/834,151.
Office action dated Aug. 8, 2017 for U.S. Appl. No. 14/814,935.

* cited by examiner

METHODS AND SYSTEMS TO FORM PROPYLENE CHLOROHYDRIN FROM DICHLOROPROPANE USING LEWIS ACID

CROSS-REFERENCE TO RELATED APPLICATIONS

This application claims benefit of U.S. Provisional Application No. 62/678,038, filed May 30, 2018, which is incorporated herein by reference in its entirety in the present disclosure.

BACKGROUND

Polyurethane production remains one of the environmentally challenging manufacturing processes in industrial polymerization. Formed from addition reactions of di-isocyanates and polyols, polyurethanes may have a significant embedded environmental footprint because of the challenges associated with both feedstocks. Polyols are themselves polymerization derivatives which use propylene oxide as raw materials. Traditionally, propylene oxide (PO) may be synthesized from a chlorinated intermediate, propylene chlorohydrin. However, an environmentally acceptable process for the economic production of propylene oxide remains elusive. High costs of chlorine and significant waste water production (approximately 40 tonnes of waste water per tonne of PO) has caused manufacturers to look for process options with reduced environmental and safety risks.

SUMMARY

Provided herein are methods and systems related to hydrolyze dichloropropane (DCP) to propylene chlorohydrin (PCH) in a solution comprising Lewis acid and then convert PCH to propylene oxide (PO) in high yields and with high selectivity and significantly less side products and/or waste materials.

In one aspect, there are provided methods to form PCH, comprising: hydrolyzing DCP to PCH in an aqueous solution comprising Lewis acid.

In one aspect, there are provided methods to form PCH, comprising:

(i) chlorinating propylene to result in one or more products comprising DCP;

(ii) separating the one or more products comprising DCP; and (iii) hydrolyzing the DCP to PCH in an aqueous solution comprising Lewis acid.

In some embodiments of the foregoing aspect, the method further comprises chlorinating the propylene with chlorine. In some embodiments of the foregoing aspect and embodiments, the method further comprises electrochemically producing the chlorine before chlorinating the propylene with the chlorine.

In one aspect, there are provided methods to form PCH, comprising:

(i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode;

(ii) withdrawing the anode electrolyte from the electrochemical cell and chlorinating propylene with the anode electrolyte comprising metal chloride with metal ion in higher oxidation state and the saltwater to result in one or more products comprising DCP, and the metal chloride with the metal ion in lower oxidation state;

(iii) separating the one or more products comprising DCP from aqueous medium; and (iv) hydrolyzing the DCP to PCH in an aqueous solution comprising Lewis acid.

In one aspect, there are provided methods to form PCH, comprising:

(i) electrochemically producing chlorine (e.g. chlor-alkali process);

(ii) using the chlorine to chlorinate propylene to result in one or more products comprising DCP;

(iii) separating the one or more products comprising DCP; and (iv) hydrolyzing the DCP to PCH in an aqueous solution comprising Lewis acid.

In one aspect, there are provided methods to form PCH, comprising:

(i) oxychlorinating metal ion of metal chloride from lower oxidation state to higher oxidation state in presence of an oxidant;

(ii) chlorinating propylene with the metal chloride with metal ion in the higher oxidation state to result in one or more products comprising DCP and the metal chloride with the metal ion in the lower oxidation state;

(iii) separating the one or more products comprising DCP; and (iv) hydrolyzing the DCP to PCH in an aqueous solution comprising Lewis acid.

In some embodiments of the above noted aspects, the Lewis acid is selected from the group consisting of silicon chloride; germanium chloride; tin chloride; boron chloride; aluminum chloride; gallium chloride; indium chloride; thallium chloride; phosphorus chloride; antimony chloride; arsenic chloride; copper chloride; zinc chloride; titanium chloride; vanadium chloride; chromium chloride; manganese chloride; iron chloride; cobalt chloride; nickel chloride; lanthanide chloride; and triflates. In some embodiments of the above noted aspects and embodiments, the Lewis acid is selected from the group consisting of $SiCl_4$; $GeCl_4$; $SnCl_4$; $BCl_3$; $AlCl_3$; $GaCl_3$; $InCl_3$; $TlCl_3$; $PCl_3$; $SbCl_3$; $AsCl_3$; $CuCl_2$; $ZnCl_2$; $TiCl_3$; $TiCl_4$; $VCl_4$; $CrCl_2$; $MnCl_2$; $FeCl_2$; $FeCl_3$; $CoCl_2$; $NiCl_2$; $LaCl_3$; $Zn(OTf)_2$; and $Sc(OTf)_3$. In some embodiments of the above noted aspects and embodiments, the Lewis acid is selected from the group consisting of $BCl_3$; $AlCl_3$; $GaCl_3$; $InCl_3$; $TlCl_3$; $CuCl_2$; $ZnCl_2$; $TiCl_3$; $TiCl_4$; and $LaCl_3$. In some embodiments of the above noted aspects and embodiments, the Lewis acid is $AlCl_3$; $GaCl_3$; $CuCl_2$; or $ZnCl_2$. In some embodiments of the above noted aspects and embodiments, the Lewis acid is in a concentration in a range of about 0.1-6 mol/kg of the solution.

In some embodiments of the above noted aspects and embodiments, the aqueous solution further comprises HCl. In some embodiments of the above noted aspects and embodiments, the HCl is other HCl added to the hydrolysis step (the "other HCl" has been described herein) and/or HCl co-produced during the hydrolysis step. In some embodiments of the above noted aspects and embodiments, the HCl is in a concentration of between about 1-20 wt % or 2-20 wt % HCl.

In some embodiments of the above noted aspects and embodiments, the aqueous solution further comprises one or more chloride salts. In some embodiments of the above noted aspects and embodiments, the one or more chloride salts are alkali metal chloride and/or alkaline earth metal chloride. In some embodiments of the above noted aspects and embodiments, the one or more chloride salts are sodium chloride, lithium chloride, potassium chloride, calcium chloride, magnesium chloride, barium chloride, strontium chloride, or combination thereof. In some embodiments of the above noted aspects and embodiments, the one or more chloride salts are in a concentration of between about 1-30 wt %.

In some embodiments of the above noted aspects and embodiments, concentration of the DCP in the hydrolysis reaction is between about 10-95% by volume.

In some embodiments of the above noted aspects and embodiments, the method further comprises carrying out the hydrolysis in reaction conditions selected from temperature between 20° C.-200° C., pressure between 0-350 psig, residence time of less than two hours, and combinations thereof.

In some embodiments of the above noted aspects and embodiments, the hydrolysis results in PCH formed with selectivity of between 10-95 wt % and/or STY of more than 0.01.

In some embodiments of the above noted aspects and embodiments, where the chlorination of the propylene is with the metal chloride with metal ion in the higher oxidation state, the method further comprises after the separation, transferring the aqueous medium comprising the metal chloride with metal ions in the higher oxidation state and the lower oxidation state to the electrochemical reaction and/or the oxychlorination reaction and oxidizing the metal ion of the metal chloride from the lower oxidation state to the higher oxidation state.

In some embodiments of the above noted aspects and embodiments, the oxidant is HCl and oxygen, or hydrogen peroxide (or any other oxidant described herein). In some embodiments of the above noted aspects and embodiments, the method further comprises forming HCl by the hydrolysis of the DCP to the PCH; separating the HCl; and transferring the HCl to the oxychlorination reaction and/or adding other HCl to the oxychlorination reaction. The other HCl has been described herein. In some embodiments of the above noted aspects and embodiments, the method further comprises recirculating the metal chloride with the metal ion in the higher oxidation state back to the chlorination reaction and/or the electrochemical reaction.

In some embodiments of the above noted aspects and embodiments, the separation of the one or more products comprising DCP comprises extraction using DCP as an extraction solvent. In some embodiments of the above noted aspects and embodiments, the DCP as the extraction solvent is the DCP separated and recirculated from the same process and/or is other DCP from other sources (the other DCP has been described herein).

In some embodiments of the above noted aspects and embodiments, the method further comprises adding other DCP as an extraction solvent to the chlorination reaction for the extraction of the one or more products; to the hydrolysis reaction for the extraction of the DCP and the PCH; and/or to the epoxidation reaction for the extraction of the DCP and the PCH (the epoxidation reaction is described herein).

In some embodiments of the above noted aspects and embodiments, the method further comprises after hydrolysis, transferring the solution comprising PCH and DCP to epoxidation; and epoxidizing the PCH with a base to form PO in presence of the DCP. In some embodiments of the above noted aspects and embodiments, the base is selected from alkali metal hydroxide, alkali metal oxide, alkaline earth metal hydroxide, or alkaline earth metal oxide.

In some embodiments of the above noted aspects and embodiments, the base is metal hydroxychloride species of stoichiometry $M_x^{n+}Cl_y(OH)_{(nx-y)}$, such as, for example only, $Cu_xCl_y(OH)_{(2x-y)}$. In some embodiments of the above noted aspects and embodiments, metal in the metal hydroxychloride is same as metal in the metal chloride. In some embodiments of the above noted aspects and embodiments, the method further comprises forming the metal hydroxychloride by oxychlorinating the metal chloride with the metal ion in the lower oxidation state to the higher oxidation state in presence of water and oxygen. In some embodiments of the above noted aspects and embodiments, the base is between about 5-38 wt %.

In some embodiments of the above noted aspects and embodiments, the reaction forms between about 5-42 tonnes of brine per tonne of PO.

In some embodiments of the above noted aspects and embodiments, metal ion in the metal chloride is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments of the above noted aspects and embodiments, the metal chloride is copper chloride.

In one aspect, there are provided systems, comprising reactors configured to carry out the reactions of the preceding aspects and embodiments.

In one aspect, there are provided systems to form PCH, comprising: a hydrolysis reactor comprising DCP in an aqueous solution comprising Lewis acid, wherein the reactor is configured to hydrolyze the DCP to PCH.

In one aspect, there are provided systems to form PCH, comprising:

(i) an electrochemical cell comprising an anode chamber comprising an anode and an anode electrolyte wherein the anode electrolyte comprises metal chloride and saltwater and the anode is configured to oxidize the metal chloride with metal ion in a lower oxidation state to a higher oxidation state; a cathode chamber comprising a cathode and a cathode electrolyte; and a voltage source configured to apply voltage to the anode and the cathode;

(ii) a chlorination reactor operably connected to the anode chamber of the electrochemical cell and configured to obtain the anode electrolyte and chlorinate propylene with the anode electrolyte comprising the metal chloride with the metal ion in the higher oxidation state in the saltwater to result in one or more products comprising DCP and the metal chloride with the metal ion in the lower oxidation state; and (iii) a hydrolysis reactor operably connected to the chlorination reactor and configured to obtain the one or more products comprising DCP from the chlorination reactor and configured to hydrolyze the DCP to the PCH in an aqueous solution comprising Lewis acid.

In one aspect, there are provided systems to form PCH, comprising: (i) a chlorination reactor configured to chlorinate propylene to result in one or more products comprising DCP; and (ii) a hydrolysis reactor operably connected to the chlorination reactor and configured to obtain the one or more products comprising DCP from the chlorination reactor and configured to hydrolyze the DCP to the PCH in an aqueous solution comprising Lewis acid. In some embodiments of the foregoing aspect, the chlorination reactor is operably connected to an electrochemical cell configured to produce chlorine (e.g. chlor-alkali process) and the chlorination reactor is configured to chlorinate the propylene with the chlorine. In some embodiments of the foregoing aspect, the chlorination reactor and/or the hydrolysis reactor is operably connected to a traditional chlorohydrin system and is configured to obtain other DCP from the traditional chlorohydrin system.

In some embodiments of the foregoing aspect, the system further comprises an oxychlorination reactor such that the system comprises (i) oxychlorination reactor configured to oxidize metal chloride with metal ion in lower oxidation state to higher oxidation state using an oxidant; (ii) chlorination reactor operably connected to the oxychlorination reactor configured to obtain the metal chloride with metal ion in the higher oxidation state and chlorinate propylene with the metal chloride with the metal ion in the higher oxidation state to result in one or more products comprising DCP and the metal chloride with the metal ion in the lower oxidation state; and (iii) a hydrolysis reactor operably connected to the chlorination reactor and configured to obtain the one or more products comprising DCP from the chlorination reactor and configured to hydrolyze the DCP to PCH in an aqueous solution comprising Lewis acid. The oxidants have been described herein. In some embodiments, the oxychlorination reactor is operably connected to both the chlorination reactor and/or the hydrolysis reactor and is configured to obtain aqueous medium from the chlorination reactor comprising the metal chloride with metal ion in the lower oxidation state and the higher oxidation state and/or obtain HCl produced in the hydrolysis reactor and is configured to oxidize the metal chloride with metal ion in the lower oxidation state to the higher oxidation state using an oxidant comprising the HCl and oxygen.

In some embodiments of the above noted aspects and embodiments, the Lewis acid is selected from the group consisting of silicon chloride; germanium chloride; tin chloride; boron chloride; aluminum chloride; gallium chloride; indium chloride; thallium chloride; phosphorus chloride; antimony chloride; arsenic chloride; copper chloride; zinc chloride; titanium chloride; vanadium chloride; chromium chloride; manganese chloride; iron chloride; cobalt chloride; nickel chloride; lanthanide chloride; and triflates. In some embodiments of the above noted aspects and embodiments, the Lewis acid is selected from the group consisting of $SiCl_4$; $GeCl_4$; $SnCl_4$; $BCl_3$; $AlCl_3$; $GaCl_3$; $InCl_3$; $TlCl_3$; $PCl_3$; $SbCl_3$; $AsCl_3$; $CuCl_2$; $ZnCl_2$; $TiCl_3$; $TiCl_4$; $VCl_4$; $CrCl_2$; $MnCl_2$; $FeCl_2$; $FeCl_3$; $CoCl_2$; $NiCl_2$; $LaCl_3$; $Zn(OTf)_2$; and $Sc(OTf)_3$. In some embodiments of the above noted aspects and embodiments, the Lewis acid is selected from the group consisting of $BCl_3$; $AlCl_3$; $GaCl_3$; $InCl_3$; $TlCl_3$; $CuCl_2$; $ZnCl_2$; $TiCl_3$; $TiCl_4$; and $LaCl_3$. In some embodiments of the above noted aspects and embodiments, the Lewis acid is $AlCl_3$; $GaCl_3$; $CuCl_2$; or $ZnCl_2$.

In some embodiments of the above noted aspects and embodiments, the Lewis acid is in a concentration in a range of about 0.1-6 mol/kg of the solution.

In some embodiments of the above noted aspects and embodiments, the aqueous solution further comprises HCl. In some embodiments of the above noted aspects and embodiments, the HCl is in a concentration of between about 1-20 wt % HCl.

In some embodiments of the above noted aspects and embodiments, the aqueous solution further comprises one or more chloride salts. In some embodiments of the above noted aspects and embodiments, the one or more chloride salts are alkali metal chloride and/or alkaline earth metal chloride. In some embodiments of the above noted aspects and embodiments, the one or more chloride salts are sodium chloride, lithium chloride, potassium chloride, calcium chloride, magnesium chloride, barium chloride, strontium chloride, or combination thereof. In some embodiments of the above noted aspects and embodiments, the one or more chloride salts are in a concentration between about 1-30 wt %.

In some embodiments of the above noted aspects and embodiments, concentration of the DCP in the hydrolysis reactor is between about 10-95% by volume.

In some embodiments of the above noted aspects and embodiments, the hydrolysis reactor is configured to carry out the hydrolysis reaction in reaction conditions selected from temperature between 20° C.-200° C., pressure between 0-350 psig, residence time of less than two hours, and combinations thereof.

In some embodiments of the above noted aspects and embodiments, the system further comprises an epoxidation reactor operably connected to the hydrolysis reactor and configured to obtain the solution comprising DCP and PCH and epoxidize the PCH to PO in presence of a base. In some embodiments, the base is selected from alkali metal hydroxide, alkali metal oxide, alkaline earth metal hydroxide, and alkaline earth metal oxide. In some embodiments, the base is NaOH, CaO, or $Ca(OH)_2$.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

DETAILED DESCRIPTION

Figure 1:
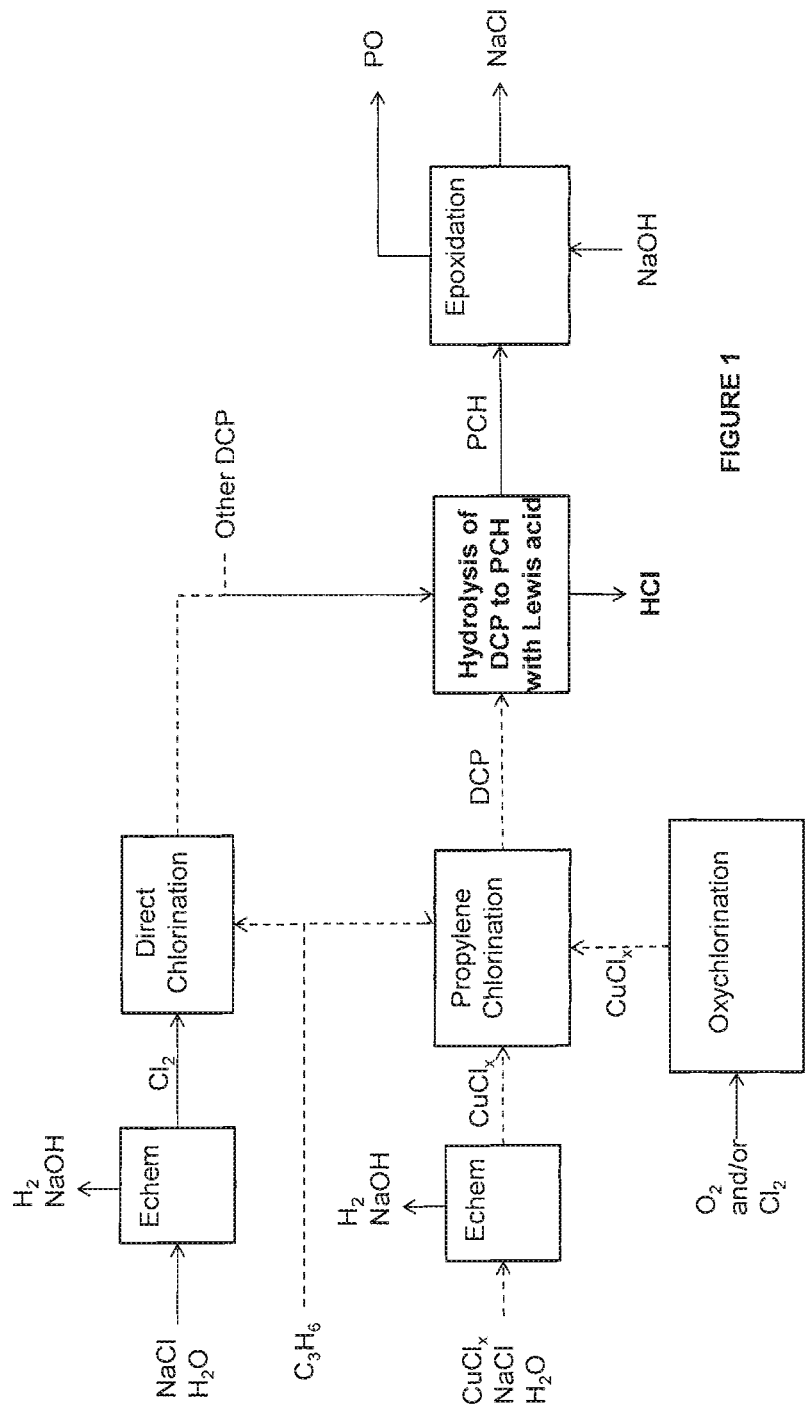
FIG. 1 is an illustration of some embodiments related to the methods and systems provided herein to form the PCH from the DCP using Lewis acid.

Disclosed herein are systems and methods that relate to producing the PCH with high selectivity and in high yield by hydrolysis of the DCP using Lewis acid and further form the PO from the PCH with high selectivity and significantly less side products and/or waste materials.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numericals. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods and Systems

There are provided methods and systems that relate to the hydrolysis of the DCP to the PCH in high yield and with high selectivity using Lewis acid. In one aspect, there is provided a method to form PCH, comprising: hydrolyzing the DCP to the PCH using the Lewis acid.

The DCP may be formed by various individual or combined chlorination reactions/systems including, but are not limited to, the chlorination of propylene using metal chloride with metal ions in the higher oxidation state for the generation of one or more products comprising DCP along with reduction of the metal chloride to metal ions in lower oxidation state; the DCP formed as a by-product of other processes, such as the traditional chlorohydrin route to the PO; and/or production of the DCP through the direct addition of chlorine to the propylene. Various other methods/systems to form the DCP are known and can be integrated with the hydrolysis reaction/system provided herein. The "1,2-dichloropropane" or "dichloropropane" or "propylene dichloride" or "DCP" or "PDC" can be used interchangeably. The "propylene chlorohydrin" or "PCH", as used herein includes PCH in its isomeric form, such as, 1-chloro-2-propanol, 2-chloro-1-propanol, or both. Without being limited by any theory, both isomers may be formed and both may be subsequently converted to the PO. The explicit declaration of one isomer may not be construed as the absence of the other. It is to be understood that the chlorination methods/systems to form the DCP may also form the PCH and other side products, such as, but not limited to, isopropyl chloride and/or isopropanol. The side products may be converted back to the DCP, the PCH, and/or the propylene. In some embodiments, a mixture of the DCP and the PCH may be subjected to the hydrolysis step so that the DCP is hydrolyzed to the PCH. All of these methods may contribute to achieving high yield and high selectivity of the PCH and therefore, high yield and high selectivity of the PO formed from the PCH.

The combination of the methods and systems to form the DCP from the propylene and further to form the PCH and the PO relate to various combinations of an electrochemical method/system, a chlorination method/system, an oxychlorination method/system, a hydrolysis method/system, and an epoxidation method/system, to form the PO. The electrochemical, the chlorination, the oxychlorination, the hydrolysis, and the epoxidation methods and systems have been described in U.S. patent application Ser. No. 15/963,637, filed Apr. 26, 2018; and U.S. patent application Ser. No. 15/992,422, filed May 30, 2018, which are both incorporated herein by reference in their entireties. Provided herein are the combinations of the electrochemical, the chlorination, the oxychlorination, and the epoxidation methods/systems integrated with the hydrolysis methods/systems.

Hydrolysis Reaction/System to Hydrolyze DCP to PCH Using Lewis Acid

Figure 2:
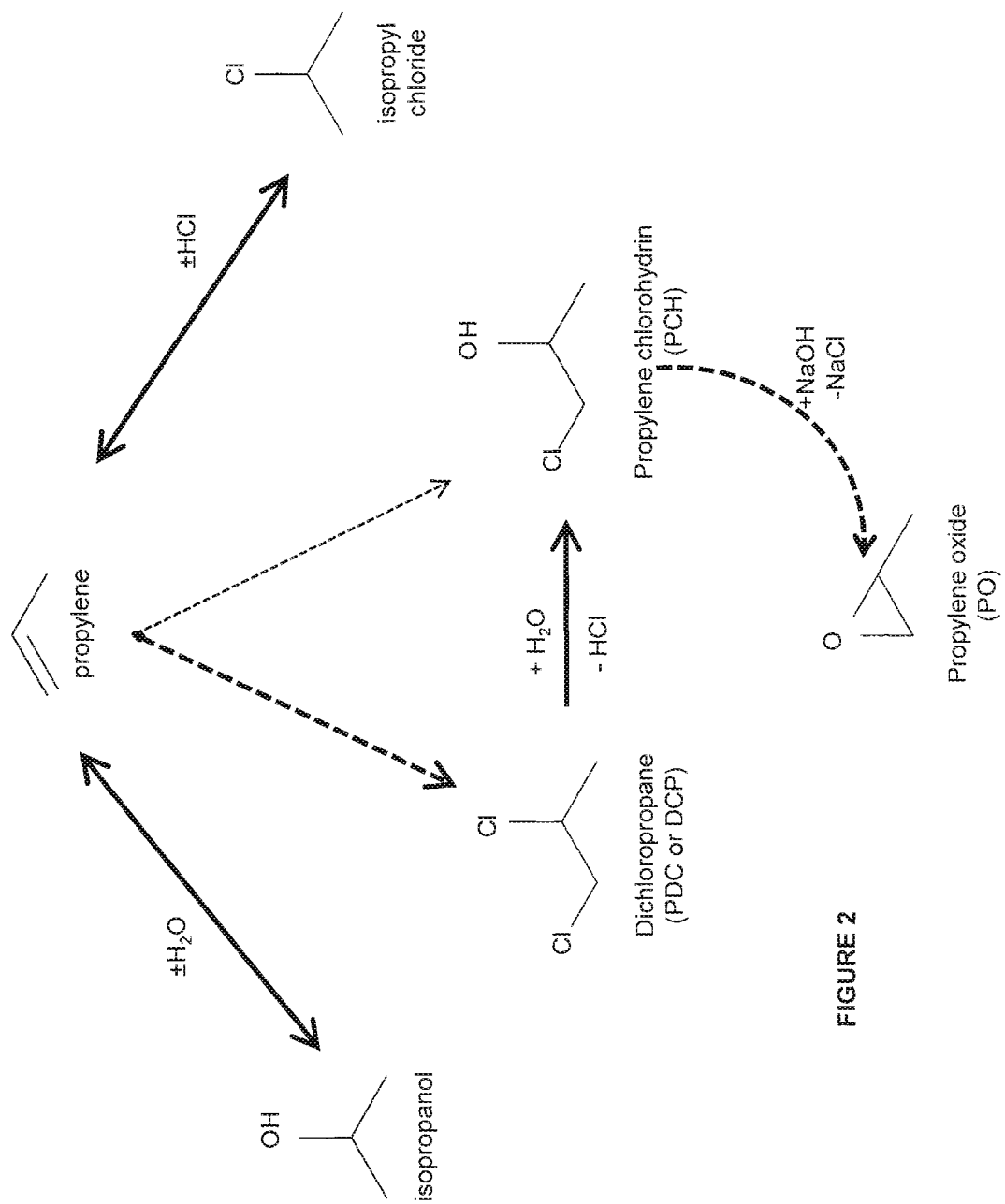
FIG. 2 is an illustration of some embodiments related to the formation of products from chlorination of propylene.

Illustrated in FIG. 1 is the block flow diagram for the formation of the PO from the propylene via the hydrolysis of the DCP to the PCH. As illustrated, the chlorination of the propylene forms one or more products comprising DCP. Various chlorinated products that may be formed by the chlorination of the propylene are illustrated in FIG. 2 and include, without limitation, the PCH, the isopropyl chloride and/or the isopropanol. The DCP is then hydrolyzed to the PCH using the Lewis acid. The PCH can be then epoxidized to the PO in the presence of a base.

The conversion of the DCP to the PCH is a hydrolysis reaction:

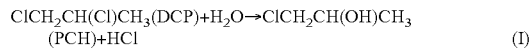

(I)

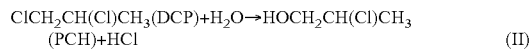

(II)

In reactions (I) and (II) above, the DCP is hydrolyzed using the Lewis acid into the PCH: the two isomers of the PCH include 1-chloro-2-propanol and 2-chloro-1-propanol. Typically, the hydrolysis reaction may be slow. Applicants have found that the use of Lewis acid in the hydrolysis reaction can result in high yield and high selectivity of the PCH. To capture the full value, the methods provided herein hydrolyze the DCP to the PCH in a way that provides a high STY (space time yield to minimize reactor costs) with high selectivity (to minimize propylene costs) and allows for recovery of the co-produced HCl (to reduce the need for both chlorine production and alkalinity consumption to neutralize the acid), as described further herein.

The "Lewis acid" as used herein includes any conventional Lewis acid capable of accepting an electron pair. Without limitation, Lewis acids herein include hard acids and soft acids. Examples include, but are not limited to, silicon chloride, e.g. $SiCl_4$; germanium chloride, e.g. $GeCl_4$; tin chloride, e.g. $SnCl_4$; boron halides, e.g. boron chloride, such as $BCl_3$; aluminum halides, e.g. aluminum chloride, such as $AlCl_3$; gallium halides, e.g. gallium chloride, such as $GaCl_3$; indium halide, e.g. $InCl_3$; thallium halide, e.g. $TlCl_3$; phosphorus chloride, e.g. $PCl_3$; antimony chloride, e.g. $SbCl_3$; arsenic chloride, e.g. $AsCl_3$; copper halide, e.g. copper chloride, such as $CuCl_2$; zinc halide, e.g. zinc chloride, such as $ZnCl_2$; titanium chloride, e.g. $TiCl_3$ or $TiCl_4$; vanadium chloride, e.g. $VCl_4$; chromium chloride, e.g. $CrCl_2$; manganese chloride, e.g. $MnCl_2$; iron chloride, e.g. $FeCl_2$ or $FeCl_3$; cobalt chloride, e.g. $CoCl_2$; or nickel chloride, e.g. $NiCl_2$. The Lewis acid also includes, but is not limited to, lanthanide chloride selected from lanthanum chloride, cerium chloride, praseodymium chloride, neodymium chloride, promethium chloride, samarium chloride, europium chloride, gadolinium chloride, terbium chloride, dysprosium chloride, holmium chloride, erbium chloride, thulium chloride, ytterbium chloride, or lutetium chloride. The Lewis acid also includes, but is not limited to, triflates, e.g. scandium triflate, e.g. $Sc(OTf)_3$ or zinc triflate, e.g. $Zn(OTf)_2$—where Tf=triflate; $SO_3CF_3$.

In some embodiments, the Lewis acid is selected from silicon chloride; germanium chloride; tin chloride; boron chloride; aluminum chloride; gallium chloride; indium chloride; thallium chloride; phosphorus chloride; antimony chloride; arsenic chloride; copper chloride; zinc chloride; titanium chloride; vanadium chloride; chromium chloride; manganese chloride; iron chloride; cobalt chloride; nickel chloride; lanthanide chloride; and triflate. In some embodiments, the Lewis acid is selected from $SiCl_4$; $GeCl_4$; $SnCl_4$; $BCl_3$; $AlCl_3$; $GaCl_3$; $InCl_3$; $TlCl_3$; $PCl_3$; $SbCl_3$; $AsCl_3$; $CuCl_2$; $ZnCl_2$; $TiCl_3$; $TiCl_4$; $VCl_4$; $CrCl_2$; $MnCl_2$; $FeCl_2$; $FeCl_3$; $CoCl_2$; $NiCl_2$; $LaCl_3$; $Zn(OTf)_2$; and $Sc(OTf)_3$. In some embodiments, the Lewis acid is selected from $BCl_3$; $AlCl_3$; $GaCl_3$; $InCl_3$; $TlCl_3$; $CuCl_2$; $ZnCl_2$; $TiCl_3$; $TiCl_4$; and $LaCl_3$. In some embodiments, the Lewis acid is $AlCl_3$; $GaCl_3$; $CuCl_2$; or $ZnCl_2$. In some embodiments, the Lewis acid is $ZnCl_2$.

In some embodiments, the Lewis acid may be replaced by Bronsted acid for the hydrolysis of the DCP to the PCH. The "Bronsted acid" as used herein, includes any compound that can transfer a proton to any other compound. Examples of the Bronsted acid, include, but are not limited to, heteropoly acids, such has, $H_3PMo_{12}O_{40}$; $H_3PW_{12}O_{40}$; $H_3PMo_6V_6O_{40}$; $H_4XM_{12}O_{40}$ where X=Si or Ge and M=Mo or W; $H_3XM_{12}O_{40}$ where X=P or As and M=Mo or W; or $H_6X_2M_{18}O_{62}$ where X=P or As and M=Mo or W. The symbols of the chemical elements are well known in the art. All the aspects and embodiments related to the Lewis acid can be applied to the Bronsted acid and as such all are within the scope of the invention.

In some embodiments of the foregoing aspect and embodiments, the Lewis acid herein is used as an aqueous solution of the Lewis acid. Accordingly, in some embodiments of the foregoing aspects and embodiments, there are provided methods to form PCH, comprising: hydrolyzing DCP to PCH in an aqueous solution comprising Lewis acid. In some embodiments, the Lewis acid concentration is in a range of about 0.1-6 mol/kg of the solution. In some embodiments, the Lewis acid is in a concentration in a range of about 0.1-6 mol/kg; or about 0.1-5.5 mol/kg; or about 0.1-5 mol/kg; or about 0.1-4.5 mol/kg; or about 0.1-4 mol/kg; or about 0.1-3.5 mol/kg; or about 0.1-3 mol/kg; or about 0.1-2.5 mol/kg; or about 0.1-2 mol/kg; or about 0.1-1.5 mol/kg; or about 0.1-1 mol/kg; or about 0.1-0.5 mol/kg; or about 0.5-6 mol/kg; or about 0.5-5 mol/kg; or about 0.5-4 mol/kg; or about 0.5-3 mol/kg; or about 0.5-2 mol/kg; or about 0.5-1 mol/kg; or about 1-6 mol/kg; or about 1-5 mol/kg; or about 1-4 mol/kg; or about 1-3 mol/kg; or about 1-2 mol/kg; or about 2-6 mol/kg; or about 2-5 mol/kg; or about 2-4 mol/kg; or about 2-3 mol/kg; or about 3-6 mol/kg; or about 3-5.5 mol/kg; or about 3-5 mol/kg; or about 3-4.5 mol/kg; or about 3-4 mol/kg; or about 4-6 mol/kg; or about 4-5.5 mol/kg; or about 4-5 mol/kg; or about 5-6 mol/kg of the solution. For example only, in some embodiments, the Lewis acid selected from $SiCl_4$; $GeCl_4$; $SnCl_4$; $BCl_3$; $AlCl_3$; $GaCl_3$; $InCl_3$; $TlCl_3$; $PCl_3$; $SbCl_3$; $AsCl_3$; $CuCl_2$; $ZnCl_2$; $TiCl_3$; $TiCl_4$; $VCl_4$; $CrCl_2$; $MnCl_2$; $FeCl_2$; $FeCl_3$; $CoCl_2$; $NiCl_2$; $LaCl_3$; and $Sc(OTf)_3$ is in a concentration in a range of about 0.1-6 mol/kg of the solution.

In some embodiments of the foregoing aspects and embodiments, hydrochloric acid (HCl) can improve the yield and/or the selectivity of the PCH during the hydrolysis of the DCP using Lewis acid. In some embodiments of the foregoing aspects and embodiments, addition of the HCl can improve the recovery of the HCl from the solution. Accordingly, in some embodiments of the foregoing aspects and embodiments, there are provided methods to form PCH, comprising: hydrolyzing DCP to PCH in an aqueous solution comprising Lewis acid and HCl. The HCl may be added to the hydrolysis reaction/reactor (the "other HCl" as explained herein) in addition to the co-produced HCl that is retained in the reactor (as shown in equations I and II above). The hydrolysis reaction may be carried out in the presence of between about 1-20 wt % HCl; or between about 2-20 wt % HCl; or between about 5-20 wt % HCl; or between about 8-20 wt % HCl; or between about 10-20 wt % HCl; or between about 15-20 wt % HCl; or between about 10-15 wt % HCl; or between about 3-15 wt % HCl; or between about 4-10 wt % HCl.

In some embodiments, there are provided methods to form PCH, comprising: hydrolyzing the DCP to the PCH in an aqueous solution comprising Lewis acid in concentration of between about 0.1-6 mol/kg of the solution and HCl in concentration of between about 1-20 wt %. In some embodiments, there are provided methods to form PCH, comprising: hydrolyzing the DCP to the PCH in an aqueous solution comprising $ZnCl_2$ in concentration of between about 0.1-6 mol/kg of the solution and HCl in concentration of between about 1-20 wt %.

In some embodiments, there are provided methods to form PCH, comprising: hydrolyzing the DCP to the PCH in an aqueous solution comprising Lewis acid in concentration of about 0.1-6 mol/kg; or about 0.1-5.5 mol/kg; or about 0.1-5 mol/kg; or about 0.1-4.5 mol/kg; or about 0.1-4 mol/kg; or about 0.1-3.5 mol/kg; or about 0.1-3 mol/kg; or about 0.1-2.5 mol/kg; or about 0.1-2 mol/kg; or about 0.1-1.5 mol/kg; or about 0.1-1 mol/kg; or about 0.1-0.5 mol/kg; or about 0.5-6 mol/kg; or about 0.5-5 mol/kg; or about 0.5-4 mol/kg; or about 0.5-3 mol/kg; or about 0.5-2 mol/kg; or about 0.5-1 mol/kg; or about 1-6 mol/kg; or about 1-5 mol/kg; or about 1-4 mol/kg; or about 1-3 mol/kg; or about 1-2 mol/kg; or about 2-6 mol/kg; or about 2-5 mol/kg; or about 2-4 mol/kg; or about 2-3 mol/kg; or about 3-6 mol/kg; or about 3-5.5 mol/kg; or about 3-5 mol/kg; or about 3-4.5 mol/kg; or about 3-4 mol/kg; or about 4-6 mol/kg; or about 4-5.5 mol/kg; or about 4-5 mol/kg; or about 5-6 mol/kg, of the solution; and HCl in concentration of between about 1-20 wt %; or between about 2-20 wt % HCl; or between about 5-20 wt % HCl; or between about 8-20 wt % HCl; or between about 10-20 wt % HCl; or between about 15-20 wt % HCl; or between about 10-15 wt % HCl; or between about 3-15 wt % HCl; or between about 4-10 wt % HCl. Any combination of the concentration of the Lewis acid and the HCl can be employed and all are within the scope of the invention.

In some embodiments of the foregoing aspect and embodiments, the hydrolysis reaction of the DCP to make the PCH using the Lewis acid is carried out in conditions that allow for the recovery of the HCl. For example, the recovered HCl can be recycled to facilitate other chemical processes such as oxychlorination of CuCl to $CuCl_2$, which can then be used for further conversion of the propylene (described in detail herein). To recover the co-produced HCl in an economic manner it may be recoverable in a concentrated form such that the produced HCl can be removed through vaporization without significant cost (as the HCl may be recovered from the vapor leaving the reactor). Because the HCl and water may form a high boiling azeotrope, it may be valuable to find a reactor composition whereby the vapor phase concentration of the HCl is near or above this threshold. This may be accomplished by two variables: elevated HCl concentration and/or elevated chloride salt concentration. Increasing HCl concentration in the aqueous phase can increase the HCl concentration in the vapor phase. As described above, the HCl may be added to the hydrolysis reaction/reactor in addition to the co-produced HCl that is retained in the reactor.

The chloride salts, as noted above, may bind to free water molecules so that the vapor phase HCl concentration may increase. The high chloride salt concentration may be achieved by using high Lewis acid concentration when the Lewis acid is a chloride salt (e.g. zinc chloride, aluminum chloride etc.). In some embodiments, one or more chloride salt(s) may be added to the hydrolysis reaction. The "chloride salt" as used herein includes alkali metal chloride or alkaline earth metal chloride. Examples include, without limitation, sodium chloride, lithium chloride, potassium chloride, calcium chloride, magnesium chloride, barium chloride, strontium chloride, etc.

In some embodiments of the foregoing aspect and embodiments, there are provided methods to form PCH, comprising: hydrolyzing DCP to PCH in an aqueous solution comprising Lewis acid and one or more chloride salts. In some embodiments, the aqueous solution comprising Lewis acid and one or more chloride salts, further comprises the HCl.

In some embodiments, there are provided methods to form PCH, comprising: hydrolyzing DCP to PCH in an aqueous solution comprising Lewis acid in concentration of between about 0.1-6 mol/kg of the solution; and one or more chloride salts in concentration of between about 1-30 wt %. In some embodiments, there are provided methods to form PCH, comprising: hydrolyzing DCP to PCH in an aqueous solution comprising Lewis acid in concentration of between about 0.1-6 mol/kg of the solution; HCl in concentration of between about 1-20 wt % or 2-20 wt %; and one or more chloride salts in concentration of between about 1-30 wt %.

In some embodiments, there are provided methods to form PCH, comprising: hydrolyzing DCP to PCH in an aqueous solution comprising $ZnCl_2$ in concentration of between about 0.1-6 mol/kg of the solution; and one or more chloride salts in concentration of between about 1-30 wt %. In some embodiments, there are provided methods to form PCH, comprising: hydrolyzing DCP to PCH in an aqueous solution comprising $ZnCl_2$ in concentration of between about 0.1-6 mol/kg of the solution; HCl in concentration of between about 1-20 wt % or 2-20 wt %; and one or more chloride salts in concentration of between about 1-30 wt %.

In some embodiments, there are provided methods to form PCH, comprising: hydrolyzing DCP to PCH in an aqueous solution comprising Lewis acid in concentration of between about 0.1-6 mol/kg of the solution; and an alkaline earth metal chloride e.g. calcium chloride or alkali metal chloride, e.g. sodium chloride in concentration of between about 1-30 wt %. In some embodiments, there are provided methods to form PCH, comprising: hydrolyzing DCP to PCH in an aqueous solution comprising Lewis acid in concentration of between about 0.1-6 mol/kg of the solution; HCl in concentration of between about 1-20 wt %; and an alkaline earth metal chloride e.g. calcium chloride or alkali metal chloride, e.g. sodium chloride in concentration of between about 1-30 wt %.

In some embodiments, there are provided methods to form PCH, comprising: hydrolyzing DCP to PCH in an aqueous solution comprising $ZnCl_2$ in concentration of between about 0.1-6 mol/kg of the solution; and an alkaline earth metal chloride e.g. calcium chloride or alkali metal chloride, e.g. sodium chloride in concentration of between about 1-30 wt %. In some embodiments, there are provided methods to form PCH, comprising: hydrolyzing DCP to PCH in an aqueous solution comprising $ZnCl_2$ in concentration of between about 0.1-6 mol/kg of the solution; HCl in concentration of between about 1-20 wt %; and an alkaline earth metal chloride e.g. calcium chloride or alkali metal chloride, e.g. sodium chloride in concentration of between about 1-30 wt %.

In some embodiments, the one or more chloride salts (for example only, sodium chloride and/or calcium chloride) in the hydrolysis reaction include between about 1-30 wt % salt; or between 1-25 wt % salt; or between 1-20 wt % salt; or between 1-10 wt % salt; or between 5-30 wt % salt; or between 5-20 wt % salt; or between 5-10 wt % salt; or between about 8-30 wt % salt; or between about 8-25 wt % salt; or between about 8-20 wt % salt; or between about 8-15 wt % salt; or between about 10-30 wt % salt; or between about 10-25 wt % salt; or between about 10-20 wt % salt; or between about 10-15 wt % salt; or between about 15-30 wt % salt; or between about 15-25 wt % salt; or between about 15-20 wt % salt; or between about 20-30 wt % salt; or between about 20-25 wt % salt.

In some embodiments of the foregoing aspect and embodiments, reaction conditions for the hydrolysis reaction comprise temperature between 120-160° C., pressure between 125-350 psig or 0-350 psig, or combination thereof. In some embodiments, the temperature of the hydrolysis reaction/reactor is between 20° C.-200° C. or between 90° C.-160° C.

In some embodiments, the water in the hydrolysis reaction is between 5-50%; or 5-40%; or 5-30%; or 5-20%; or 5-10%; or 50-75%; or 50-70%; or 50-65%; or 50-60% by weight.

In some embodiments, the hydrolysis reaction conditions in the methods to form the PCH comprise varying the residence time of the hydrolysis solution. The "incubation time" or "residence time" or "mean residence time" as used herein includes the time period for which the hydrolysis solution is left in the reactor at the above noted temperatures before being taken out for the separation of the product. In some embodiments, the residence time for the hydrolysis solution is few seconds or between about 1 sec-1 hour; or 1 sec-5 hours; or 10 min-5 hours or more depending on the temperature of the hydrolysis solution. This residence time may be in combination with other reaction conditions such as, e.g. the temperature ranges and/or chloride concentrations provided herein. In some embodiments, the residence time for the hydrolysis solution is between about 1 sec-3 hour; or between about 1 sec-2.5 hour; or between about 1 sec-2 hour; or between about 1 sec-1.5 hour; or between about 1 sec-1 hour; or 10 min-3 hour; or between about 10 min-2.5 hour; or between about 10 min-2 hour; or between about 10 min-1.5 hour; or between about 10 min-1 hour; or between about 10 min-30 min; or between about 20 min-3 hour; or between about 20 min-2 hour; or between about 20 min-1 hour; or between about 30 min-3 hour; or between about 30 min-2 hour; or between about 30 min-1 hour; or between about 1 hour-2 hour; or between about 1 hour-3 hour; or between about 2 hour-3 hour, to form the PCH as noted herein. In some embodiments, the residence time in the hydrolysis reaction/reactor is less than two hours or less than one hour.

In some embodiments of the foregoing aspect and embodiments, the hydrolysis of the DCP to the PCH in the aqueous Lewis acid solution and optionally HCl and/or one or more chloride salts, may be maximized if the aqueous medium can be saturated with the DCP. In some embodiments, the DCP may be present in excess amount in order to facilitate efficient hydrolysis. In some embodiments, the DCP may be as high as 10-95% by volume; or 10-90% by volume; or 10-80% by volume; or 10-70% by volume; or 10-60% by volume; or 10-50% by volume; or 10-40% by volume; or 10-30% by volume; or 10-20% by volume; or 25-95% by volume; or 25-90% by volume; or 25-80% by volume; or 25-70% by volume; or 25-60% by volume; or 25-50% by volume; or 50-95% by volume; or 50-75% by volume; or 75-95% by volume, of the total solution volume.

The above noted DCP amount can be obtained by using the DCP stream from one chlorination reaction or from several chlorination reactions. Such chlorination reactions have been described in detail herein. The above noted amount of the DCP can form a second organic phase which may help ensure that a soluble concentration of the DCP remains in the aqueous phase. In some embodiments, further degradation of the PCH into other products (such as, but not limited to, acetone, propanal, and/or propylene glycol) may be minimized as the PCH may preferentially partition into the DCP phase rather than the aqueous phase. In a continuous operation, the PCH may be removed from the reactor in the organic phase with the un-reacted DCP. This last advantage may alleviate the need to separate the PCH from the aqueous solution by other techniques such as distillation. In some embodiments, the PCH may be extracted from the hydrolysis solution using DCP as an extraction solvent (described in detail herein). By extracting the PCH with the DCP, the PCH can be removed from the chlorination reactor by removing the DCP layer that is phase-separated from the aqueous layer.

In some embodiments of all of the aspect and embodiments provided herein, the PCH is formed with selectivity of between about 10-100%; or between about 10-90%; or between about 10-80%; or between about 10-70%; or between about 10-60%; or between about 10-50%; or between about 10-40%; or between about 10-30%; or between about 10-20%; or between about 5-10%; or between about 20-100%; or between about 20-90%; or between about 20-80%; or between about 20-70%; or between about 20-60%; or between about 20-50%; or between about 20-40%; or between about 30-100%; or between about 30-90%; or between about 30-80%; or between about 30-70%; or between about 30-60%; or between about 30-50%; or between about 30-40%; or between about 40-100%; or between about 40-90%; or between about 40-80%; or between about 40-70%; or between about 40-60%; or between about 40-50%; or between about 75-100%; or between about 75-90%; or between about 75-80%; or between about 90-100%; or between about 90-99%; or between about 90-95%. In some embodiments, the above noted selectivity is in wt %.

In some embodiments, the STY of the PCH is 0.01, or more than 0.01, or more than 0.05, or 0.1, or more than 0.1, or more than 0.5, or is 1, or more than 1, or more than 2, or more than 3, or between 0.1-3, or between 0.01-0.05, or between 0.05-0.1, or between 0.1-1, or between 0.1-0.5, or between 0.5-3, or between 0.5-2, or between 0.5-1, or between 3-5. As used herein the STY is yield per time unit per reactor volume. For example, the yield of product may be expressed in mol, the time unit in hour and the volume in liter. The volume may be the nominal volume of the reactor, e.g. in a packed bed reactor, the volume of the vessel that holds the packed bed is the volume of the reactor. The STY may also be expressed as STY based on the amount of DCP consumed to form the product. For example only, in some embodiments, the STY of the PCH product may be deduced from the amount of DCP consumed during the reaction. The selectivity may be the mol of product, e.g. PCH/mol of the DCP consumed. The yield may be the amount of the product isolated. The purity may be the amount of the product/total amount of all products (e.g., amount of PCH/all the organic products formed).

In some embodiments of the foregoing aspect and embodiments, the reaction of the DCP with water to make the PCH can also be improved with conditions that favor the DCP solubility in water. For example, co-solvents may help increase the DCP-water interactions and thus reaction kinetics. Co-solvents can be ones that are soluble in both water and the DCP or that promote the DCP solubility in water.

Hydrolysis Reaction/System Integrated with Other Reactions/Systems

The Lewis acid containing hydrolysis reaction/system provided herein may be integrated with any number of method/systems forming the DCP from the propylene and further forming the PO from the PCH.

Electrochemical, Chlorination, and Other Reaction/Systems

Various reaction/systems integrated with the chlorination reactions/systems to form the DCP from the propylene are shown in FIG. 1 in dotted lines. For example, the DCP may be formed by a combination of an electrochemical reaction coupled with propylene chlorination reaction. The electrochemical reaction/cell comprises the metal ions of the metal halide in the lower oxidation state and the higher oxidation state, illustrated as $CuCl_x$ (a mixture of CuCl and $CuCl_2$). The metal ions are oxidized from the lower oxidation state to the higher oxidation state at the anode where cathode reaction includes formation of an alkali metal hydroxide, e.g. sodium hydroxide. The anode electrolyte comprising $CuCl_x$ is then transferred to the chlorination reaction where the propylene gets chlorinated by the metal halide with metal ion in the higher oxidation state forming one or more products comprising DCP and the reduced metal ions (metal halide in the lower oxidation state). Other cathode reaction are also possible and are explained in detail in U.S. patent application Ser. No. 15/963,637, filed Apr. 26, 2018, which is incorporated herein by reference in its entirety. For example, in some embodiments, the cathode electrolyte comprises water and the cathode is an oxygen depolarizing cathode that reduces oxygen and water to hydroxide ions; the cathode electrolyte comprises water and the cathode is a hydrogen gas producing cathode that reduces water to hydrogen gas and hydroxide ions; the cathode electrolyte comprises hydrochloric acid and the cathode is a hydrogen gas producing cathode that reduces hydrochloric acid to hydrogen gas; or the cathode electrolyte comprises hydrochloric acid and the cathode is an oxygen depolarizing cathode that reacts hydrochloric acid and oxygen gas to form water.

The "metal ion" or "metal" or "metal ion in the metal chloride" or "metal ion in the metal halide" as used herein, includes any metal ion capable of being converted from lower oxidation state to higher oxidation state and vice versa. Examples of metal ions in the metal halide include, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ions include, but not limited to, iron, copper, tin, chromium, or combination thereof. In some embodiments, the metal ion is copper. In some embodiments, the metal ion is tin. In some embodiments, the metal ion is iron. In some embodiments, the metal ion is chromium. In some embodiments, the metal ion is platinum. The "oxidation state" as used herein, includes degree of oxidation of an atom in a substance. For example, in some embodiments, the oxidation state is the net charge on the metal ion. The "halide" as used herein, includes fluoride, bromide, chloride, and iodide. For example only, metal halide includes metal chlorides such as, but not limited to, copper chloride (CuCl with Cu in the lower oxidation state of 1 and $CuCl_2$ with Cu in the higher oxidation state of 2). As used herein, the "salt" or "saltwater" includes salt or salt in water where salt can be any alkali metal chloride or alkaline earth metal chloride, including but not limited to, sodium chloride, potassium chloride, lithium chloride, calcium chloride, magnesium chloride etc.

It is to be understood that the metal chloride with the metal ion in the lower oxidation state and the metal chloride with the metal ion in the higher oxidation state are both present in the aqueous medium in the chlorination reaction. Owing to the reduction of the metal chloride from the higher oxidation state to the lower oxidation state in the chlorination reaction, the ratio of the metal chloride in the lower and the higher oxidation state are different in the aqueous medium entering the chlorination reaction and exiting the chlorination reaction. Suitable concentrations of the metal ions in the lower and higher oxidation state in the aqueous medium have been described herein. Some examples of the metal chlorides that may be used in the systems and methods include, but are not limited to, copper chloride, iron chloride, tin chloride, chromium chloride, zinc chloride, etc.

The anolyte from the anode chamber containing an aqueous stream of sodium chloride (any other salt may be used including but not limited to, alkali metal chloride such as potassium chloride or alkaline earth metal chloride such as calcium chloride), water and $CuCl_x$ is transferred to the chlorination reaction/reactor. In the chlorination reaction/reactor, the propylene $C_3H_6$ is converted into the DCP and optionally the other products using copper (II) chloride, simultaneously reducing two Cu(II) ions to Cu(I). The reactions are as shown below:

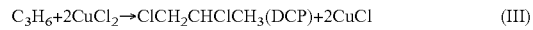

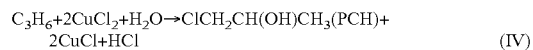

An illustration of the chlorination reaction is shown in FIG. 2 where the chlorination of propylene forms DCP and without limitation, other products, such as PCH, isopropyl chloride, and isopropanol. In some embodiments, the propylene may be supplied under pressure in the liquid phase and/or the gas phase and the metal chloride, for example only, copper (II) chloride (also containing copper (I) chloride) is supplied in an aqueous solution such as saltwater. The reaction may occur in the liquid phase where the dissolved propylene reacts with the copper (II) chloride. As illustrated in FIG. 2, the chlorination of the propylene in the presence of the metal chloride with the metal ion in the higher oxidation state (e.g. $CuCl_2$) may result in one or more products such as, but not limited to, the PCH, the DCP, the isopropanol, and the isopropyl chloride.

In some embodiments, the DCP can be sourced into the hydrolysis reaction as a by-product of other processes, such as direct chlorination of propylene or traditional chlorohydrin process. For example, FIG. 1 illustrates a stream of the DCP from the direct addition of chlorine to the propylene (shown in dotted lines). New or existing sources of chlorine (such as, but not limited to, Deacon process and the chlor-alkali process (shown in FIG. 1 as electrochemical reaction/ cell forming $Cl_2$) may be used to make the DCP via direct chlorination of the propylene, similar to the process used industrially to make ethylene dichloride from ethylene and chlorine. This DCP formed via direct chlorination may then be hydrolyzed to the PCH (shown in dotted lines) and/or may be sent to the propylene chlorination reaction/system (shown again in dotted lines). These DCP streams from other processes are also labeled as the "other DCP" in FIGS. 1, 3 and 4, which illustrate the various locations in the process where this stream may be incorporated into the process. The incorporation of this other DCP can lead to additional PCH and PO production thus upgrading these streams to more valuable products.

In the traditional chlorohydrin process, the PCH may be formed through the addition of hypochlorous acid (HOCl) to the propylene. The HOCl may itself be formed by the addition of chlorine ($Cl_2$) to water, a reaction which co-produces a stoichiometric amount of hydrochloric acid (HCl). To minimize reactions of the propylene with both HCl and the direct addition of $Cl_2$ across the double bond, the reactor may be operated under very dilute concentrations of HOCl and with an equivalent of base (in the form of NaOH or CaO) to neutralize the HCl. Even under these conditions, the formation of unwanted DCP can be significant, representing a propylene selectivity loss on the order of 10%. This unwanted DCP can also be used as the "other DCP" in the methods described herein and provide an economic use of a waste stream.

Such methods and systems for various sources of DCP may be integrated with the hydrolysis methods and systems provided herein to hydrolyze the DCP (formed as a major product or as a waste stream) to the PCH using the Lewis acid and then to the PO.

Accordingly, in one aspect, there are provided methods to form PCH, comprising:

(i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode;

(ii) withdrawing the anode electrolyte from the electrochemical cell and chlorinating propylene with the anode electrolyte comprising metal chloride with metal ion in higher oxidation state and the saltwater to result in one or more products comprising DCP, and the metal chloride with the metal ion in lower oxidation state;

(iii) separating the one or more products comprising DCP from aqueous medium; and (iv) hydrolyzing the DCP to PCH in an aqueous solution comprising Lewis acid.

In one aspect, there are provided methods to form PCH, comprising:

(i) using chlorine to chlorinate propylene to result in one or more products comprising DCP;

(ii) separating the one or more products comprising DCP; and (iii) hydrolyzing the DCP to PCH in an aqueous solution comprising Lewis acid.

In one aspect, there are provided methods to form PCH, comprising:

(i) electrochemically producing chlorine (e.g. chlor-alkali process);

(ii) using the chlorine to chlorinate propylene to result in one or more products comprising DCP;

(iii) separating the one or more products comprising DCP; and (iv) hydrolyzing the DCP to PCH in an aqueous solution comprising Lewis acid.

In the aspects noted above, the one or more products obtained after the chlorination may further comprise PCH, isopropyl chloride, and/or isopropanol (as shown in FIG. 2). The isopropyl chloride, and/or isopropanol may be converted back to the DCP, the PCH and/or the propylene. The isopropyl chloride and/or the isopropanol may be sourced from other processes as waste streams and converted to valuable products. In some embodiments, the DCP may be formed in high yield in chlorination and may then be hydrolyzed to the PCH. There may be a number of options to increase the rate and/or selectivity of the DCP formation. These options include highly concentrated salt solutions which reduce the available free water. Because water is a reactant in the hydrolysis of the DCP to the PCH, the presence of free water may lead to the conversion of the DCP to the PCH. The high concentrations of salt may be accomplished through the addition of the copper chloride salts (such as $CuCl_2$, CuCl or in combination) or through other salts such as NaCl. There are also a number of process conditions which can be optimized to provide higher STY and higher selectivity for the DCP production including temperature, pressure (e.g. pressures under which the propylene may form a liquid or supercritical phase), and residence time.

In one aspect, there is provided a system comprising a hydrolysis reactor configured to obtain one or more products comprising DCP from a chlorination reactor and configured to hydrolyze the DCP to PCH using an aqueous solution of Lewis acid.

In one aspect, there is provided a system comprising (i) an electrochemical cell comprising an anode chamber comprising an anode and an anode electrolyte wherein the anode electrolyte comprises metal chloride and saltwater and anode is configured to oxidize metal chloride with metal ion in a lower oxidation state to a higher oxidation state; a cathode chamber comprising a cathode and a cathode electrolyte; and a voltage source configured to apply voltage to the anode and the cathode; (ii) a chlorination reactor operably connected to the anode chamber of the electrochemical cell and configured to obtain the anode electrolyte and chlorinate propylene with the anode electrolyte comprising the metal chloride with the metal ion in the higher oxidation state in the saltwater to result in one or more products comprising DCP and the metal chloride with the metal ion in the lower oxidation state; (iii) a hydrolysis reactor operably connected to the chlorination reactor and configured to obtain the one or more products comprising DCP from the chlorination reactor and configured to hydrolyze the DCP to the PCH using an aqueous solution of Lewis acid; and (iv) an epoxidation reactor operably connected to the hydrolysis reactor and configured to obtain the solution comprising DCP and PCH and epoxidize the PCH to PO in presence of a base. In some embodiments, the system further comprises an oxychlorination reactor operably connected to the chlorination reactor and/or the hydrolysis reactor and configured to obtain aqueous medium from the chlorination reactor comprising the metal chloride with metal ion in the lower oxidation state and the higher oxidation state and/or obtain HCl produced in the hydrolysis reactor and configured to oxidize the metal chloride with metal ion in the lower oxidation state to the higher oxidation state using an oxidant comprising the HCl and oxygen (illustrated in FIGS. 3 and 4). The oxychlorination reaction/system has been described further herein.

Figure 3:
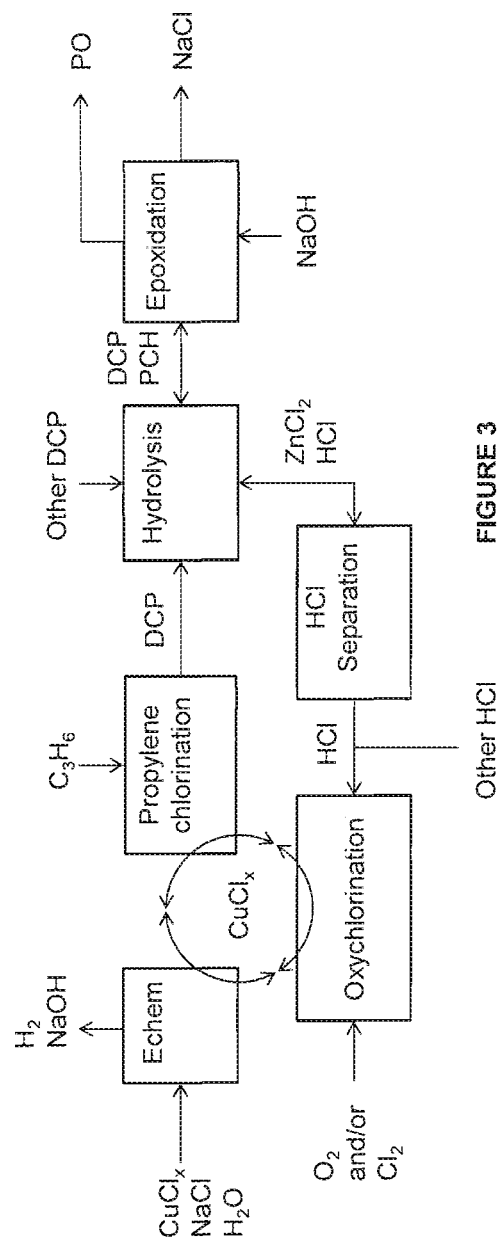
FIG. 3 is an illustration of some embodiments related to the methods and systems provided herein to form the PCH and the PO.

In some embodiments, the chlorination reaction/system may be followed by a separation step/system to separate the one or more products comprising DCP (and optionally comprising PCH and other side products) from the aqueous medium before hydrolyzing the DCP to the PCH using the Lewis acid. The hydrolysis of the DCP to the PCH may be executed in a second reaction step downstream (in a separate reactor) of the propylene chlorination. Illustrated in FIG. 3 is an aspect where the DCP is converted to the PCH in a hydrolysis reaction/reactor after the chlorination reaction/reactor. FIG. 3 illustrates embodiments where the propylene chlorination, after the electrochemical reaction, results in one or more products comprising the DCP (and optionally the PCH). The DCP separated from the chlorination is then sent to the hydrolysis reaction where the DCP is hydrolyzed to the PCH in an aqueous solution comprising the Lewis acid. The other DCP may be added to the hydrolysis reaction to use the waste streams. To leverage the process economics of the conversion of the DCP to the PCH in an optimum way, the process may recover at least some of the HCl by-product from the hydrolysis of the DCP to the PCH. This HCl can be reused in a traditional oxychlorination reaction for the production of ethylene dichloride (EDC) or used in the oxychlorination within the process, as shown with circular arrows in FIG. 3 and described further herein.

In some embodiments, the step of separating the one or more products comprising DCP from the chlorination reaction comprises any separation method known in the art. In some embodiments, the one or more products comprising DCP and optionally the PCH may be separated from the chlorination reaction as a vapor stream. The separated vapors may be cooled and/or compressed and subjected to the hydrolysis reaction. Other separation methods include, without limitation, distillation and/or flash distillation using the distillation column or flash distillation column. The remaining one or more products comprising DCP and optionally the PCH in the aqueous medium may be further separated using methods such as, decantation, extraction, or combination thereof. Various examples of the separation methods are described in detail in U.S. patent application Ser. No. 14/446,791, filed Jul. 30, 2014, which is incorporated herein by reference in its entirety.

In one aspect, the DCP may be used as an extraction solvent that can extract the DCP and the PCH from the aqueous stream from the chlorination reaction/reactor. The DCP used as the extraction solvent can be DCP from the same process that has been separated and recirculated and/or is the other DCP. The other DCP has been described herein. Without limitation, the extraction solvent can be any organic solvent that removes the DCP and/or the PCH from the aqueous metal ion solution.

Figure 4:
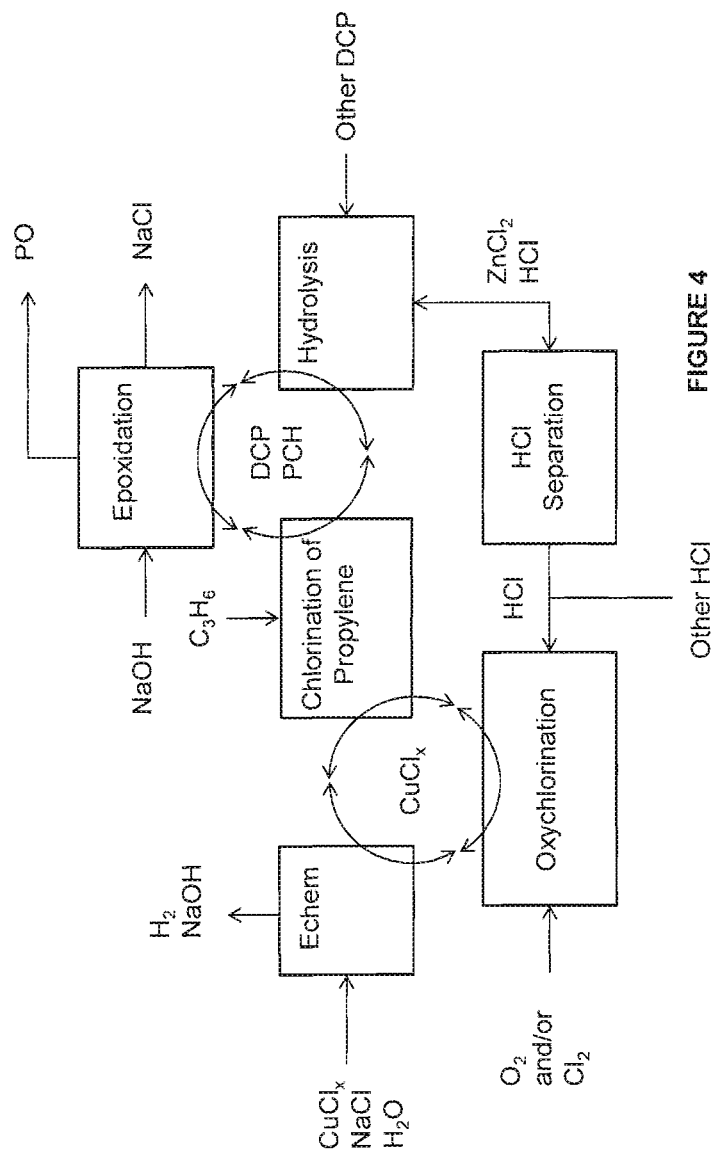
FIG. 4 is an illustration of some embodiments related to the methods and systems provided herein to form the PCH and the PO.

FIG. 4 illustrates an example of the use of the DCP as the extracting solvent. In FIG. 4, the recirculating DCP stream serves to extract the DCP and the PCH both from the propylene chlorination reaction/reactor and the hydrolysis reaction/reactor. The PCH recovered from these reactors along with the DCP may be then sent to epoxidation, where the PCH is converted to the PO and the un-reacted DCP stream is separated and recirculated. In this configuration, any DCP made in the propylene chlorination reactor may be balanced by conversion to the PCH in the hydrolysis reactor. The extracting solvent, as shown in FIG. 4 by circular arrows, can flow either clockwise or counterclockwise. The order of operations may be determined by process economics. The epoxidation of the PCH to the PO in the presence of the DCP has been described herein.

Accordingly, in one aspect, there are provided methods to form PCH, comprising: hydrolyzing DCP to PCH in an aqueous solution comprising Lewis acid and extracting the DCP and the PCH from the aqueous solution by extracting with DCP as an extraction solvent.

In one aspect, there are provided methods to form PCH, comprising: (i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode; (ii) withdrawing the anode electrolyte from the electrochemical cell and chlorinating propylene in the anode electrolyte comprising metal chloride with metal ion in higher oxidation state to result in one or more products comprising DCP and PCH, and the metal chloride with the metal ion in lower oxidation state; (iii) extracting the one or more products comprising DCP and PCH from the aqueous medium using DCP as an extraction solvent; and (iv) hydrolyzing the DCP to the PCH in an aqueous solution of Lewis acid. In some embodiments, the method further includes after extraction, transferring aqueous medium comprising the metal chloride with metal ions in the higher oxidation state and the lower oxidation state to the oxychlorinating and/or electrochemical step.

In some embodiments, the temperature and the residence time in the hydrolysis reaction/reactor may be different from the one in the chlorination reaction/reactor. For example, in some embodiments, the hydrolysis reaction may be run at a lower temperature than the chlorination reaction. Also, in some embodiments, the residence time in the hydrolysis reaction may be longer than that in the chlorination reaction. The extraction method may be such that once the one or more products comprising DCP and PCH are extracted from the aqueous medium using the DCP as an extraction solvent, the organics are transferred to the hydrolysis reaction; the aqueous stream comprising metal chloride with metal ions in the higher oxidation state and the lower oxidation state is added back to the electrochemical reaction and/or the oxychlorination reaction; and the hydrolysis reaction is run at lower temperature and longer residence time so that the DCP is hydrolyzed to the PCH using the Lewis acid. This may avoid more DCP being formed and/or more PCH decomposing to form other side products in the chlorination reaction.

In some embodiments of the above noted aspect, the method further includes transferring the organic medium comprising PCH and DCP (remaining if any, after the hydrolyis) from the hydrolyzing step to epoxidation; and epoxidizing the PCH with a base to form PO in the presence of the DCP (described further herein).

In some embodiments of the above noted aspects, the PCH formed after the hydrolysis step may be extracted from the aqueous medium again using the DCP as an extraction solvent. In some embodiments, where the DCP is used as an extraction solvent for the PCH, the DCP may be separated from the PCH and the separated DCP may be recirculated to the separation reaction/reactor and/or to the hydrolysis reaction/reactor.

Oxychlorination Reaction/System

In some embodiments, the chlorination reaction/reactor and the hydrolysis reaction/reactor may be integrated with an oxychlorination reaction/reactor, as illustrated by dotted arrows in FIG. 1. It is to be understood that each of the dotted arrows in FIG. 1 represent separate embodiments as well as combined embodiments. For example, in some embodiments, the oxychlorination reaction/reactor is combined with the chlorination method/reactor, the hydrolysis reaction/reactor, and the epoxidation reaction/reactor, absent any electrochemical reaction/cell. In some embodiments, the oxychlorination reaction/reactor is combined with the electrochemical reaction/cell, the chlorination reaction/reactor, the hydrolysis reaction/reactor, and the epoxidation reaction/reactor, as shown in FIGS. 3 and 4. In some embodiments, the electrochemical reaction/cell is combined with the chlorination method/reactor, the hydrolysis reaction/reactor, and the epoxidation reaction/reactor, absent any oxychlorination reaction/reactor, as shown in FIG. 1. In some embodiments, the electrochemical reaction/cell containing the metal halide with metal ion in the lower and higher oxidation state is combined with the chlorination method/reactor, the hydrolysis reaction/reactor, and the epoxidation reaction/reactor, as shown in FIG. 1. In some embodiments, the electrochemical reaction/cell producing chlorine gas is combined with the chlorination method/reactor, the hydrolysis reaction/reactor, and the epoxidation reaction/reactor, as shown in FIG. 1. In some embodiments, the electrochemical reaction/cell containing the metal halide with metal ion in the lower and higher oxidation state; the electrochemical reaction/cell producing chlorine gas; and the oxychlorination reaction/reactor are all combined with the chlorination method/reactor, the hydrolysis reaction/reactor, and the epoxidation reaction/reactor, as shown in FIG. 1. Therefore, the electrochemical reaction/cell and the oxychlorination reaction/reactor may individually be combined with the other systems and/or combined with each other and the other systems. All of such combinations are well within the scope of the invention.

Accordingly, in one aspect, there are provided methods to form PCH, comprising:

(i) oxychlorinating metal ion of metal chloride from lower oxidation state to higher oxidation state in presence of an oxidant;

(ii) chlorinating propylene with the metal chloride with metal ion in the higher oxidation state to result in one or more products comprising DCP and the metal chloride with the metal ion in the lower oxidation state;

(iii) separating the one or more products comprising DCP; and (iv) hydrolyzing the DCP to PCH in an aqueous solution comprising Lewis acid.

In some embodiments of the foregoing aspect, the separation step includes extraction with the DCP (as described above).

In one aspect, the methods/systems comprising the electrochemical reaction/cell; the chlorination reaction/reactor; and the hydrolysis reaction/reactor, may be integrated with an oxychlorination reaction/reactor as illustrated in FIGS. 3 and 4. In some embodiments of the foregoing aspects and embodiment including electrochemical reaction/cell, the method further comprises, after the separation, transferring the aqueous medium comprising the metal chloride with the metal ion in the lower oxidation state and the salt to an oxychlorination reaction and oxidizing the metal ion from the lower oxidation state to the higher oxidation state in the presence of an oxidant, such as, but not limited to, HCl and oxygen, or hydrogen peroxide or any other oxidant described herein.

In some embodiments the system comprises (i) oxychlorination reactor configured to oxidize metal chloride with metal ion in lower oxidation state to higher oxidation state using an oxidant; (ii) chlorination reactor operably connected to the oxychlorination reactor configured to obtain the metal chloride with metal ion in the higher oxidation state and chlorinate propylene with the metal chloride with the metal ion in the higher oxidation state to result in one or more products comprising DCP and the metal chloride with the metal ion in the lower oxidation state; and (iii) a hydrolysis reactor operably connected to the chlorination reactor and configured to obtain the one or more products comprising DCP from the chlorination reactor and configured to hydrolyze the DCP to PCH in an aqueous solution comprising Lewis acid.

In some embodiments, some of the Cu(I) produced in the chlorination reaction/reactor is regenerated to Cu(II) by chemical oxidation in oxychlorination reaction/reactor using oxidant such as, but not limited to, $X_2$ gas alone; or HX gas and/or HX solution in combination with gas comprising oxygen or ozone; or hydrogen peroxide; or HXO or salt thereof; or $HXO_3$ or salt thereof; or $HXO_4$ or salt thereof; or combinations thereof, wherein each X independently is a halogen selected from fluorine, chlorine, iodine, and bromine.

For example, chlorine gas may be used to oxidize the metal halide from the lower to the higher oxidation state. For example, CuCl may be oxidized to $CuCl_2$ in the presence of chlorine gas as follows:

$$2CuCl + Cl_2 \rightarrow 2CuCl_2 \quad (V)$$

In some embodiments, the oxidant is HCl gas and/or HCl solution in combination with gas comprising oxygen. An example is as follows:

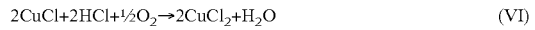

$$2CuCl + 2HCl + \tfrac{1}{2}O_2 \rightarrow 2CuCl_2 + H_2O \quad (VI)$$

In some embodiments, the oxidant is HX gas and/or HX solution in combination with hydrogen peroxide, wherein X is a halogen. One example is as follows:

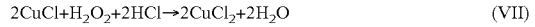

$$2CuCl + H_2O_2 + 2HCl \rightarrow 2CuCl_2 + 2H_2O \quad (VII)$$

Oxidants have been described in detail in U.S. patent application Ser. No. 15/963,637, filed Apr. 26, 2018, which is incorporated herein by reference in its entirety. The oxidants in the oxychlorination reaction/reactor oxidize the metal halide with metal ion in the lower oxidation state (such as CuCl) to the metal halide with metal ion in the higher oxidation state (such as $CuCl_2$).

Hydrochloric acid (HCl) is a common by-product in numerous chemical processes. One side product of the hydrolysis reaction of the DCP to the PCH is also HCl. The methods and systems provided herein can leverage the HCl in the oxychlorination step as a mechanism to provide additional metal oxidation. The HCl can also be sourced from other reactions and is labeled as "other HCl" in figures. The incorporation of the HCl from the chlorination reaction or other reactions may lead to additional PO production by upgrading these streams to more valuable products. The reuse of the HCl in the oxychlorination process may allow for the reduction of the base consumption to neutralize the acid which may improve overall economics, especially in cases where the base could otherwise be sold. It is to be understood that the processes illustrated in FIGS. 3 and 4, such as the electrochemical reaction, the chlorination reaction, and the oxychlorination reaction, may each be individually combined with the hydrolysis reaction. For example, the electrochemically generated $CuCl_2$ may be used in one reactor for the chlorination of the propylene to the DCP and the chemically generated $CuCl_2$ (via oxychlorination) may be used in another propylene chlorination reactor each with the option of making the DCP with subsequent hydrolysis to the PCH, all such configurations are within the scope of the present disclosure.

The flow of the copper chloride between the electrochemical, the chlorination and the oxychlorination reaction/systems may be either clockwise or counter clockwise as indicated by the circular arrows in FIGS. 3 and 4. That is, the order of operations between the three units is flexible. In some embodiments of the foregoing aspect and embodiments, the method further comprises recirculating the metal chloride in the higher oxidation state from the oxychlorination reaction back to the chlorinating reaction and/or the electrochemical reaction.

Epoxidation Reaction/System

In some embodiments of the foregoing aspect and embodiments, the methods further comprise reacting the PCH with a base to form the PO. Various process configurations that lead to the epoxidation step have been described above and are illustrated in the figures herein.

The PCH in the foregoing aspects may be converted to the PO in the epoxidation reaction/reactor as illustrated in FIGS. 1-4 and shown in the reaction below.

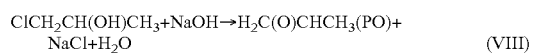

$$ClCH_2CH(OH)CH_3 + NaOH \rightarrow H_2C(O)CHCH_3(PO) + NaCl + H_2O \quad (VIII)$$

Typically, the conversion of the PCH to the PO is a ring-closing reaction whereby the chlorohydrin molecule may be combined in a near stoichiometric ratio with a base. The products are PO, the chloride salt of the base and water. Because the PO may be a reactive molecule, it may need to be removed from the reaction media quickly. Typically, the short residence time requirement may be achieved by steam stripping the PO as it is formed in the reactor. However, because the PCH feeding the reactor may be diluted with a large excess of water due to upstream reaction selectivity considerations (described further herein below), the steam demand for PO stripping may be very high.

In some aspects noted above, the methods and systems after hydrolysis, further comprise reacting the PCH with a base to form PO in presence of DCP or the methods and systems comprise reacting the solution of the PCH and the DCP with a base to form PO. In some aspects, the DCP is not separated from the PCH after the hydrolysis and the solution is directly subjected to epoxidation. In such embodiments, the separation of the DCP and the PCH step (before and/or after hydrolysis step) may be combined with the epoxidation step such that when the base is added into the epoxidation reactor, the base reacts with the PCH to form the PO, which may leave the reactor as a vapor. In this process, some DCP may be converted to the PCH which would also form the PO. In some embodiments, the residual levels of un-reacted PCH may leave the reactor in the DCP extraction solvent (DCP as an extraction solvent has been described before) and return to the process where appropriate.

The methods and systems provided herein for converting the PCH to the PO in the presence of the DCP (where the mol % of DCP is equal to or greater than the mol % of PCH) has a number of advantages. First, it may obviate the need for separation of the PCH from the DCP prior to the epoxidation. To maintain high selectivity of the PCH during the hydrolysis reaction, the DCP level may be in excess relative to the converted amount of the DCP as described above. The PCH may be separated from the DCP via a typical separation operation. If PCH were the lighter (lower boiling) component, distillation would be an option. However, because PCH is the heavier component, separation by distillation may require the excess DCP be removed in the overhead of the column which in turn may lead to prohibitive steam demand. Alternative separation technologies, such as absorption or selective permeation, may be equally prohibitive due to either capital equipment costs or operating costs. Second, because the PO may also be soluble in the DCP, the reactor may not require steam stripping inside the reactor. The PO can be removed from the reactor in the DCP phase if desired and separated downstream. Third, additional reactions may be minimized because PO may react much more slowly in the organic (DCP) phase. Finally, the total waste water demand may be significantly reduced because the water leaving the reactor would primarily be that which came in with the caustic (and low levels of soluble water with the organic phase). In some embodiments, when using NaOH as the base for the PO formation, the resulting aqueous solution may be concentrated enough in NaCl to merit removing the waste organics and using the brine back in the electrochemical cell.

In addition to the advantages described above, the conversion of the PCH to the PO in the presence of DCP (where the mol % of DCP is equal to or greater than the mol % of PCH) may also allow for process options that minimize by-product losses, such as, a single phase reactor that contains both reactants and products; minimizing by-product formation by running the reactor with a short residence time; step-wise addition of the base, such as, NaOH; and recycling of the product stream back to the reactor. The step-wise addition of the base, such as, NaOH (e.g. along a length of pipe if the reaction is done in a continuous system) may reduce the by-product formation because the aqueous salt solutions resulting from the early additions may dilute the later additions. In this way, the caustic concentrations within the aqueous phase can be more easily managed along the reactor length. The recycling of the aqueous product stream back to the reactor inlet may also minimize the base, such as NaOH, concentration in the aqueous phase. The recycling option has other advantages too. For example, the recycle stream may return salt-rich brine to the reactor. The presence of the salt may minimize the solubility of the PO in the aqueous phase which may improve reactor selectivity.

Further, the highly concentrated salt may be advantageous because the resulting brine stream exiting the epoxidation unit may serve as a feedstock for electrolysis cells after removal of the residual, soluble organics. Furthermore, the recycle of reactor outlet may allow the reactor to run in such a way as to produce a high salt concentration outlet stream without having to feed a high concentration of the base, such as, NaOH stream directly to the reactor.

In some embodiments of the foregoing aspect and embodiments, the base is an alkali metal hydroxide, such as e.g. NaOH or alkali metal oxide; alkaline earth metal hydroxide or oxide, such as e.g. $Ca(OH)_2$ or CaO.

In some embodiments of the foregoing aspect and embodiments, the base is metal hydroxide chloride (for example only, $M_x^{n+}Cl_y(OH)_{(nx-y)}$). Without being limited by any theory, it is contemplated that the metal chloride may react with water and oxygen to form metal hydroxychloride species of stoichiometry $M_x^{n+}Cl_y(OH)_{(nx-y)}$. An illustration of the reaction is as shown below (VI) taking copper chloride as an example:

$$2CuCl+H_2O+\tfrac{1}{2}O_2 \rightarrow 2CuClOH \quad (IX)$$

Where the CuClOH species represents one of many possible copper hydroxychloride species of stoichiometry $Cu_xCl_y(OH)_{(2x-y)}$. Examples of the metal hydroxychloride, without limitation include, $MoCl(OH)_3$, $MoCl_2(OH)_2$, and $MoCl_3(OH)$.

In some embodiments of the foregoing aspect and embodiments, metal in the metal hydroxychloride is same as metal in the metal chloride. In some embodiments of the foregoing aspect and embodiments, the method further comprises forming the metal hydroxychloride by oxychlorinating the metal chloride with the metal ion in the lower oxidation state to the higher oxidation state in presence of water and oxygen.

Typically, in chlorohydrin processes for the production of propylene oxide, the base may be combined and reacted with an approximately 4-5 wt % solution of propylene chlorohydrin. The propylene chlorohydrins are a mix of 1-chloro-2-propanol (approximately 85-90%) and 2-chloro-1-propanol (approximately 10-15%). The propylene oxide formation reaction, using NaOH as an example base, may be shown as below:

$$C_3H_6(OH)Cl+NaOH \rightarrow C_3H_6O(PO)+NaCl+H_2O \quad (X)$$

Propylene oxide may be rapidly stripped from the solution in either a vacuum stripper or steam stripper. A primary disadvantage of the process may be the generation of a dilute brine stream with about 3-6 wt % salt with flow rate exceeding 45 tonnes of brine per tonne of propylene oxide. The large amount of dilute brine may result in large amount of waste water. The reason for the large volume of water may be that the reactor producing the propylene chlorohydrins must operate at dilute concentrations of about 4-5 wt % propylene chlorohydrin in order to achieve high selectivity.

Applicants have discovered that using the methods provided herein that produce the PCH in high selectivity and high STY, the amount of dilute brine generated after the PO formation can be substantially reduced. In some embodiments of the foregoing aspect and embodiments, the reaction forms between about 5-42 tonnes of brine per tonne of PO which is substantially less brine compared to the brine generated in a typical PO reaction.

In one aspect, there is provided a method to form PO, comprising chlorinating propylene with an aqueous medium comprising metal chloride with metal ion in higher oxidation state and salt to result in one or more products comprising DCP, and the metal chloride with the metal ion in lower oxidation state;

separating the one or more products comprising DCP from the aqueous medium;

hydrolyzing the DCP to PCH in an aqueous solution comprising Lewis acid; and reacting the PCH with a base to form PO and brine in water.

In some embodiments of the foregoing aspect, the chlorination is preceded by the electrochemical reaction by contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode. In some embodiments of the foregoing aspect, the chlorination is preceded by the electrochemical reaction by electrochemically producing chlorine (e.g. chlor-alkali process).

In some embodiments of the foregoing aspect and embodiments, the reaction of the PCH with a base to form PO is in presence of the DCP (i.e. remaining DCP after the hydrolysis is not separated from the PCH).

In one aspect, there is provided a method to form PO, comprising reacting PCH with a base under reaction conditions to form PO in presence of DCP. In some embodiments, the reaction conditions include, without limitation, temperature in range of between 0-150° C.; or between 10-150° C.; or between 20-150° C.; or between 30-150° C.; or between 40-150° C.; or between 50-150° C.; or between 75-150° C.; or between 100-150° C.; or between 125-150° C.; or between 10-100° C.; or between 10-50° C.; or between 20-80° C.; or between 30-60° C.; or between 30-50° C.; or between 40-75° C.; or between 40-50° C. In some embodiments, the DCP present in the reaction (which may also be the un-reacted DCP in the reaction) is between about 0-60% by volume; or 0-50% by volume; or 0-40% by volume; or 0-30% by volume; or 0-20% by volume; or between about 5-60% by volume; or 5-50% by volume; or 5-40% by volume; or 5-30% by volume; or 5-20% by volume; or 5-10% by volume; or between about 10-60% by volume; or 10-50% by volume; or 10-40% by volume; or 10-30% by volume; or 10-20% by volume; or 20-60% by volume; or 20-50% by volume; or 20-40% by volume; or 20-30% by volume; or 30-60% by volume; or 30-50% by volume; or 30-40% by volume, of the total solution volume.

In some embodiments of the foregoing aspects and embodiments, the reaction forms between about 5-42 tonnes of brine per tonne of PO. In some embodiments of the foregoing aspects and embodiments, the selectivity of the PCH formed (after chlorination and hydrolysis) is between about 10-99.9 wt %. In some embodiments of the foregoing aspects and embodiments, the base is between about 5-35 wt % or between about 8-15 wt %. The bases have been described herein and include without limitation, the alkali metal hydroxide e.g. sodium hydroxide or potassium hydroxide; alkaline earth metal hydroxide e.g. calcium hydroxide or oxide e.g. CaO or MgO; or metal hydroxide chloride. The PO formation has been illustrated in figures herein.

In some embodiments of the aforementioned aspects and embodiments, the PO formed is between about 5-50 wt %; or between about 5-40 wt %; or between about 5-30 wt %; or between about 5-20 wt %; or between about 5-10 wt %; or between about 10-50 wt %; or between about 10-40 wt %; or between about 10-30 wt %; or between about 10-20 wt %; or between about 20-50 wt %; or between about 20-40 wt %; or between about 20-30 wt %; or between about 30-50 wt %; or between about 30-40 wt %; or between about 40-50 wt %.

In some embodiments of the aspects and embodiments provided herein, the PO formed is between about 1-25 wt %; or between about 2-20 wt %; or between about 3-15 wt %.

In some embodiments of the aspects and embodiments provided herein, the reaction forms between about 5-42 tonnes of brine per tonne of PO; or between about 5-40 tonnes of brine per tonne of PO; or between about 5-35 tonnes of brine per tonne of PO; or between about 5-30 tonnes of brine per tonne of PO; or between about 5-25 tonnes of brine per tonne of PO; or between about 5-20 tonnes of brine per tonne of PO; or between about 5-10 tonnes of brine per tonne of PO. In some embodiments of the aspect and embodiments provided herein, the reaction forms between about 3-40 tonnes of brine per tonne of PO; or between about 4-20 tonnes of brine per tonne of PO; or between about 4-12 tonnes of brine per tonne of PO.

In some embodiments of the aspects and embodiments provided herein, the base is between about 5-50 wt %; or between about 5-40 wt %; or between about 5-30 wt %; or between about 5-20 wt %; or between about 5-10 wt %; or between about 10-50 wt %; or between about 10-40 wt %; or between about 10-30 wt %; or between about 10-20 wt %; or between about 20-50 wt %; or between about 20-40 wt %; or between about 20-30 wt %; or between about 30-50 wt %; or between about 30-40 wt %; or between about 40-50 wt %; or between about 8-15 wt %; or between about 10-15 wt %; or between about 12-15 wt %; or between about 14-15 wt %; or between about 8-10 wt %; or between about 8-12 wt %. In some embodiments of the aspect and embodiments provided herein, the base is between about 5-38 wt %; or between about 7-33 wt %; or between about 8-20 wt %.

The methods and systems provided herein, may further include separation and/or purification methods and systems including one or more of the separation and purification of the organic products from the metal ion solution and/or the separation and purification of the organic products from each other; to improve the overall yield of the PCH, improve selectivity of the PCH, improve purity of the PCH, improve efficiency of the systems, improve ease of use of the solutions in the overall process, improve reuse of the metal solution, and/or to improve the overall economics of the process.

In some embodiments, the solution containing the one or more products and the metal chloride may be subjected to a washing step which may include rinsing with an organic solvent or passing the organic product through a column to remove the metal ions. In some embodiments, the organic products may be purified by distillation.

In one aspect, there are provided systems, comprising reactors configured to carry out the reactions of the preceding aspects and embodiments.

The systems provided herein include one or more reactors that carry out the chlorination reaction; the hydrolysis reaction; the oxychlorination reaction; and the epoxidation reaction. The "reactor" as used herein is any vessel or unit in which the reaction provided herein is carried out. For example, the chlorination reactor is configured to contact the metal chloride solution with the propylene to form the one or more products comprising DCP. The reactor may be any means for contacting the metal chloride with the propylene. Such means or such reactor are well known in the art and include, but not limited to, pipe, column, duct, tank, series of tanks, container, tower, conduit, and the like. The reactor may be equipped with one or more of controllers to control temperature sensor, pressure sensor, control mechanisms, inert gas injector, etc. to monitor, control, and/or facilitate the reaction.

In some embodiments, the reactor system may be a series of reactors connected to each other. For example, to increase the yield of the PCH, the chlorination mixture may be kept either in the same reaction vessel (or reactor), or in a second reaction vessel (hydrolysis reactor) that does not contain additional propylene. Since the PCH and/or the DCP solubility may be limited in the aqueous medium, a second reaction vessel may be a stirred tank. The stirring may increase the mass transfer rate of the PCH and/or the DCP into the aqueous medium accelerating the hydrolysis reaction to the PCH.

The reactor configuration includes, but is not limited to, design parameters of the reactor such as, e.g. length/diameter ratio, flow rates of the liquids and gases, material of construction, packing material and type of reactor such as, packed column, bubble column, or trickle-bed reactor, or combinations thereof. In some embodiments, the systems may include one reactor or a series of multiple reactors connected to each other or operating separately. The reactor may be a packed bed such as, but not limited to, a hollow tube, pipe, column or other vessel filled with packing material. The reactor may be a spray reactor. The reactor may be a trickle-bed reactor. The reactor may be a bubble column. In some embodiments, the packed bed reactor includes a reactor configured such that the aqueous medium containing the metal ions and the propylene flow counter-currently in the reactor or includes the reactor where the aqueous medium containing the metal ions flows in from the top of the reactor and the propylene gas is pressured in from the bottom. In some embodiments, in the latter case, the propylene may be fed in such a way that only when the propylene gets consumed, that more propylene flows into the reactor. The trickle-bed reactor includes a reactor where the aqueous medium containing the metal ions and the propylene flow co-currently in the reactor.

In some embodiments, the reactor may be configured for both the reaction and the separation of the products. The processes and systems described herein may be batch processes or systems or continuous flow processes or systems.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples and elsewhere, abbreviations have the following meanings:

| | |
|---|---|
| g = | gram |
| mmol = | millimole |
| mol = | mole |
| mol/kg = | mole/kilogram |
| µl = | microliter |
| ml = | milliliter |
| psi = | pounds per square inch |
| psig = | pounds per square inch guage |
| STY = | space time yield |
| umol = | micromole |

EXAMPLES

Example 1

Formation of PCH, DCP, Isopropanol and Isopropyl Chloride from Propylene Using Copper Chloride Experiment 1: A solution of $CuCl_2$ (1.0 mol/kg), CuCl (0.19 mol/kg), NaCl (0.66 mol/kg), and HCl (0.0091 mol/kg) was heated in a Parr reactor under propylene pressure to 130° C. for 15 minutes. The reactor was depressurized into a bubbler trap at 0° C. to capture volatile compounds. When the reactor was opened, the solution was extracted three times with an organic solvent, e.g. ethyl acetate or dichloromethane, which was analyzed with a gas chromatograph equipped with a mass spectrometer. A total of 11.4 umol DCP and 12.0 umol PCH were measured. The amounts of recyclable products measured were 622 umol isopropanol, 47.9 umol acetone, and 73.0 umol isopropyl chloride.

Experiment 2: A solution of $CuCl_2$ (0.71 mol/kg), CuCl (0.71 mol/kg), and NaCl (2.76 mol/kg) was heated in a Parr reactor under propylene pressure to 150° C. for 15 minutes. The reactor was depressurized into a bubbler trap at 0° C. to capture volatile compounds. When the reactor was opened, the solution was extracted three times with an organic solvent, e.g. ethyl acetate or dichloromethane, which was analyzed with a gas chromatograph equipped with a mass spectrometer. A total of 15.6 umol DCP and 62.4 umol PCH were measured. The amounts of recyclable products measured were 1087 umol isopropanol, 18.8 umol acetone, and 80.1 umol isopropyl chloride.

Example 2

Recycling of Isopropanol

A solution of $CuCl_2$ (3.0 mol/kg), CuCl (0.50 mol/kg), and NaCl (2.0 mol/kg) were heated with added isopropanol in a Parr reactor at 140° C. for 15 minutes. The reactor was constantly purged with a flow of $N_2$ into a bubbler trap at 0° C. to capture volatile compounds. When the reactor was opened, the solution was extracted three times with an organic solvent, e.g. ethyl acetate or dichloromethane, which was analyzed with a gas chromatograph equipped with a mass spectrometer. Propylene, isopropanol, isopropyl chloride, PCH, and DCP were all detected, indicating that isopropanol can be recycled and converted into desired products.

Example 3

Recycling of Isopropyl Chloride

Similar to Example 3, reaction was conducted with isopropyl chloride instead of isopropanol. The same products were observed.

Example 4

Improved Selectivity for PCH Over DCP in the Chlorination Reaction

Experiment 1: An aqueous solution of $CuCl_2$ (2.0 mol/kg) and CuCl (1.0 mol/kg) was heated in a Parr reactor under propylene pressure to 140° C. for 30 minutes. The reactor was depressurized into a bubbler trap at 0° C. to capture volatile compounds. When the reactor was opened, the solution was extracted three times with an organic solvent, e.g. ethyl acetate or dichloromethane, which was analyzed with a gas chromatograph equipped with a mass spectrometer. A total of 47 umol DCP and 229 umol PCH were measured. The amounts of recyclable products measured were 5834 umol isopropanol, 23 umol acetone, and 189 umol isopropyl chloride.

Experiment 2: An aqueous solution of $CuCl_2$ (1.0 mol/kg), CuCl (1.0 mol/kg), and NaCl (1.0 mol/kg) was heated in a Parr reactor under propylene pressure to 140° C. for 30 minutes. The reactor was depressurized into a bubbler trap at 0° C. to capture volatile compounds. When the reactor was opened, the solution was extracted three times with an organic solvent, e.g. ethyl acetate or dichloromethane, which was analyzed with a gas chromatograph equipped with a mass spectrometer. A total of 15 umol DCP and 88 umol PCH were measured. The amounts of recyclable products measured were 917 umol isopropanol, 4 umol acetone, and 35 umol isopropyl chloride.

Example 5

Lowering of Water in PO Process

A 40 wt % solution of propylene chlorohydrin is combined with a 10 wt % solution of sodium hydroxide and brine. The use of the more concentrated PCH reduces the brine effluent from 46.2 to 10.1 tonnes per tonne of propylene oxide resulting in significant cost savings for the handling of this stream. In another example, feeding a solution of PCH in DCP may lower the total water discharged to around 7 tonnes per tonne PO, which is due to the amount of water contained in the added NaOH solution.

Example 6

Formation of PO from PCH

A glass vial was loaded with 5 mL of 0.1 N NaOH and 100 ul of PCH (70% 1-chloro-2-isopropanol and 30% 2-chloro-1-propanol). The vial was stirred with a magnetic stir bar for 20 hours. Afterward, a 1 ml aliquot was extracted with 2 ml of ethyl acetate that was subsequently analyzed by gas chromatography with a mass spectrometer detector. Propylene oxide as well as both isomers of PCH was observed, as determined by their fragmentation patterns.

Example 7

Formation of PO from PCH in Presence of DCP

A 500 ml round bottom flask was charged with 99.90 g DCP, 0.933 g octane as an internal standard, and 4.764 g (50.4 mmol) PCH. The flask was equipped with a condenser on top of which was a barbed fitting with a tube that ran into a vial of ethyl acetate in ice water bath. Any gas generated and distilled through the condenser was collected in the ethyl acetate trap. The solution was brought to a boil at roughly 90° C. At specific time intervals, 4 charges each of 10 ml of 1 N NaOH (10 mmol) was added through the top of the condenser and allowed to trickle down into the hot solution. At the end of the reaction, 34.5 mmol propylene oxide and 3.0 mmol propylene glycol were measured as products, and 7.9 mmol PCH was measured as un-reacted. This correlates to 92% propylene oxide with 90% mass balance closure.

Example 8

Formation of PO from PCH in Presence of DCP

A glass vial was charged with 1900 ul DCP and 100 ul (1.2 mmol) PCH and held at room temperature. To this, 300 ul 1 N NaOH (0.3 mmol) was added and the vial was mixed vigorously. Samples from before and after the reaction showed a reduction of the PCH amount by 31% with a concomitant increase in propylene oxide.

Example 9

Hydrolysis of DCP to PCH in Presence of Lewis Acid

A glass vial was charged with 2 ml of 4 mol $ZnCl_2$/kg solution and 2 ml of DCP (20 mmol). The vial was placed into a titanium reactor that was heated at 150° C. for 15 minutes and the solution in the vial was agitated with a magnetic stir bar. After cooling the reactor and removing the glass vial, 0.2 mmol PCH was found by GC analysis.

What is claimed is:

1. A method to form propylene chlorohydrin (PCH), comprising: hydrolyzing dichloropropane (DCP) to PCH in an aqueous solution comprising Lewis acid.

2. The method of claim 1, wherein the Lewis acid is selected from the group consisting of silicon chloride; germanium chloride; tin chloride; boron chloride; aluminum chloride; gallium chloride; indium chloride; thallium chloride; phosphorus chloride; antimony chloride; arsenic chloride; copper chloride; zinc chloride; titanium chloride; vanadium chloride; chromium chloride; managanese chloride; iron chloride; cobalt chloride; nickel chloride; lanthanide chloride; and triflates.

3. The method of claim 1, wherein the Lewis acid is selected from the group consisting of $BCl_3$; $AlCl_3$; $GaCl_3$; $InCl_3$; $TlCl_3$; $CuCl_2$; $ZnCl_2$; $TiCl_3$; $TiCl_4$; and $LaCl_3$.

4. The method of claim 1, wherein the Lewis acid is $AlCl_3$; $GaCl_3$; $CuCl_2$; or $ZnCl_2$.

5. The method of claim 1, wherein the Lewis acid is in a concentration in a range of about 0.1-6 mol/kg of the solution.

6. The method of claim 1, wherein the aqueous solution further comprises HCl.

7. The method of claim 6, wherein the HCl is a combination of the other HCl added to the hydrolysis step and the HCl co-produced during the hydrolysis step.

8. The method of claim 7, wherein the HCl is in a concentration of between about 1-20 wt % HCl.

9. The method of claim 1, wherein the aqueous solution further comprises one or more chloride salts.

10. The method of claim 9, wherein the one or more chloride salts are alkali metal chloride and/or alkaline earth metal chloride.

11. The method of claim 10, wherein the one or more chloride salts are sodium chloride, lithium chloride, potassium chloride, calcium chloride, magnesium chloride, barium chloride, strontium chloride, or combination thereof.

12. The method of claim 10, wherein the one or more chloride salts are in a concentration between about 1-30 wt %.

13. The method of claim 1, wherein concentration of the DCP in the hydrolysis reaction is between about 10-95% by volume.

14. The method of claim 1, further comprising carrying out the hydrolysis in reaction conditions selected from temperature between 20° C.-200° C., pressure between 0-350 psig, residence time of less than two hours, and combinations thereof.

15. The method of claim 1, wherein the hydrolysis results in PCH formed with selectivity of between 10-95 wt % and/or STY of more than 0.01.

16. The method of claim 1, further comprising after hydrolysis, transferring the solution comprising PCH and DCP to epoxidation; and epoxidizing the PCH with a base to form PO in presence of the DCP.

17. A system to form PCH, comprising: a hydrolysis reactor comprising DCP in an aqueous solution comprising Lewis acid, wherein the reactor is configured to hydrolyze the DCP to PCH.

18. The system of claim 17, wherein the Lewis acid is selected from the group consisting of silicon chloride; germanium chloride; tin chloride; boron chloride; aluminum chloride; gallium chloride; indium chloride; thallium chloride; phosphorus chloride; antimony chloride; arsenic chloride; copper chloride; zinc chloride; titanium chloride; vanadium chloride; chromium chloride; managanese chloride; iron chloride; cobalt chloride; nickel chloride; lanthanide chloride; and triflates.

19. The system of claim 17, wherein the Lewis acid is $AlCl_3$; $GaCl_3$; $CuCl_2$; or $ZnCl_2$.

20. The system of claim 17, wherein the aqueous solution further comprises HCl.

21. The system of claim 17, wherein the aqueous solution further comprises one or more chloride salts.

22. The system of claim 21, wherein the one or more chloride salts are alkali metal chloride and/or alkaline earth metal chloride.

* * * * *